US006992070B2

(12) United States Patent
Donahue et al.

(10) Patent No.: US 6,992,070 B2
(45) Date of Patent: Jan. 31, 2006

(54) METHODS AND COMPOSITIONS FOR NUCLEIC ACID DELIVERY

(75) Inventors: J. Kevin Donahue, Towson, MD (US); Eduardo Marban, Lutherville, MD (US); Koichi Nagata, Saitama (JP); John H. Lawrence, Pennington, NJ (US)

(73) Assignee: The Johns Hopkins University, Baltimore, MD (US)

( * ) Notice: Subject to any disclaimer, the term of this patent is extended or adjusted under 35 U.S.C. 154(b) by 326 days.

(21) Appl. No.: 09/977,865

(22) Filed: Oct. 15, 2001

(65) Prior Publication Data

US 2002/0094326 A1    Jul. 18, 2002

Related U.S. Application Data

(60) Provisional application No. 60/240,231, filed on Oct. 13, 2000.

(51) Int. Cl.
*A01N 43/04* (2006.01)
*A61K 31/70* (2006.01)
*C12N 15/00* (2006.01)
*C12N 5/00* (2006.01)
*C07H 21/04* (2006.01)

(52) U.S. Cl. .................... 514/44; 435/320.1; 435/325; 536/23.1

(58) Field of Classification Search .............. 514/44; 435/320.1, 325; 536/23.1
See application file for complete search history.

(56) References Cited

U.S. PATENT DOCUMENTS

| 5,516,651 A * | 5/1996 | Goldring et al. ........... 435/69.1 |
| 6,100,270 A | 8/2000 | Campbell |
| 6,214,620 B1 | 4/2001 | Johns et al. |
| 2002/0082240 A1 * | 6/2002 | Linden et al. ............... 514/46 |
| 2002/0094326 A1 | 7/2002 | Donahue et al. |

FOREIGN PATENT DOCUMENTS

| WO | WO 96/16657 | 6/1996 |
| WO | WO 99/19792 | 4/1999 |
| WO | WO 99/31982 | 7/1999 |

OTHER PUBLICATIONS

Carson CC Sildenafil: a 4-year update in the treatment of 20 million erectile dysfunction patients, Curr. Urol. Rep. Dec.; 2003 4(6) pp488-496.*
Crocker I.C. therapeutic potential of phosphodiesterase 4 inhibitors in allergic diseases Drugs Today. Jul.; 1999 35(7): pp519-3 and DeKorte C.J. Current and emerging therapies for the management of chronic inflammation in asthma Am J. Health Syst. Pharm.*
Netherton S.J. et al. Altered PDE-e mediated cAMP hydrolysis contributes to a hypermotile phenotype in obese JCR:LA-cp rat aortic vascular smooth muscle cells:implications for diabitets associated cardiovasular diease. Diabetes. Apr.; 2002 51(4):1194 200.*
Anderson Human Gene Therapy Nature vol. 392, supp 1998 pp 25-30.*
Verma et al. Gene therapy—promises, problems and prospects Nature vol. 389 1997 pp239-242.*
Palu et al. In pursuit of new deveopments for gene therapy of human diseases J. of Biotech. vol. 68 1999 pp1-12.*
DeKorte C.J. Current and emerging therapies for the management of chronic inflammation in asthma Am J. Health Syst. Pharm Oct. 1. 2003; (60)19: pp1949-59.*
Lamping, K, et al., "Agonist-specific impairment of coronary vascular function in genetically altered, hyperlipidemic mice," *Am. J. of Phys.*, (Apr. 1999), pp. R1023-R1029, vol. 276, No. 4.
Kuwahara, A. et al., "5-HT activates nitric oxide-generating neurons to stimulate chloride secretion in guinea pig distal colon," *Am. J. Phys.*, (Oct. 1998), pp. G829-G834, vol. 275, No. 4.
Frieden, M. et al., "Effect of 5-hydroxytriptamine on the membrane potential of endothial and smooth muscle cells in the pig coronary artery," *British Journal of Pharmacology*, (1995), pp. 95-100, vol. 115, No. 1.
Reiser, G., "Nitric oxide formation caused by calcium release from internal stores in neuronal cell line in enhanced by cyclic amp," *European Journal of Pharmacology Molecular Pharmacology Section*, (1992), pp. 89-93, vol. 9, No. 1.
Katz, S. et al., "Acute type 5 phosphodiesterase inhibition with slidenafil enhances flow-mediated vasodilation in patients with chronic heart failure," *Journal of the American College of Cardiology*, (Sep. 2000), pp. 845-851, vol. 36, No. 3.
Lai, N.C. et al., "Sodium nitroprusside facilitates intracoronary gene transfer in pigs," *Faseb Journal*, (Mar. 2001), p. A100. vol. 15, No. 4.
Bilbao, R. et al., "A blood-tumor barrier limits gene transfer to the experimental liver cancer: The effect of vasoactive compounds," *Gene Therapy*, (Nov. 2000), pp. 1824-1832, vol. 7, No. 21.

(Continued)

*Primary Examiner*—James Ketter
*Assistant Examiner*—Konstantina M. Katcheves
(74) *Attorney, Agent, or Firm*—Banner & Witcoff, Ltd.

(57) ABSTRACT

The present provides methods and compositions that enable effective delivery of nucleic acids to desired cells, including to a solid organ such as a mammalian heart. The methods and compositions enable effective gene transfer and subsequent expression to a majority of cells throughout a solid organ such as the heart. Methods and compositions of the invention preferably provide enhanced vascular permeability that enables increased gene transfer to targeted cells, but without significant degradation or injury to endothelial cell layers.

37 Claims, 3 Drawing Sheets

OTHER PUBLICATIONS

Corbin, J.D., et al., "Pharmacology of Phosphodiesterase-5 Inhibitors," *IJCP*, (Jul./Aug. 2002), pp. 453-459, vol. 56, No. 6.

Eardly, I. et al., "Tadalafil (Cialis) for Men with Erectile Dysfunction," *IJCP*, (May 2002), pp. 300-304, vol. 56, No. 4.

Donahue, J.K. et al., "Ultrarapid, highly efficient viral gene transfer to the heart," *PNAS*, (Apr. 1997), pp. 4664-4668, vol. 94.

Donahue, J.K. et al., "Acceleration of widespread adenoviral gene transfer to intact rabbit hearts by coronary perfusion with low calcium and serotonin," *Gene Therapy*, (1998), pp. 630-634, vol. 5.

Hetman, J.M. et al., "Cloning and characterization of PDE7B a cAMP-specific phosphodiesterase," *PNAS*, (Jan. 2004), pp. 472-476, vol. 97, No. 1.

Nagata, K. et al., "Phosphodiesterase Inhibitor-mediated Potentiationo f Adenovirus Delivery to Myocardium," *J. Mol. Cell. Cardiol.*, (2001), pp. 575-580, vol. 33.

Sung, B. et al., "Structure of the catalytic domain of human phosphodiesterase 5 wit bound drug molecules," *Nature*, (Sep. 2003), pp. 98-102, vol. 425.

Lenhart, S.E. et al., "Preservation of myocardial function after adenoviral gene transfer in isolated myocardium," *Am. J. Physiol. Hart Circ. Physiol.*, (2000), pp. H986-H991, vol. 279.

Rotella, D., "Phosphodiesterase 5 inhibitors: Current Status and Potential Applications," *Nature*, (Sep. 2002), pp. 674-682, vol. 1.

Soderling, S.H. et al., "Cloning and characterization of a cAMP-specific cyclic nucleotide phosphodieterase," *PNAS*, (Jul. 1998), pp. 8991-8996, vol. 95.

Barr, E. et al., "Efficient catheter-mediated gene transfer into the heart using replication-defective adenovirus," *Gene Therapy*, (Jan. 1994), pp. 51-58, vol. 1, No. 1 (Abstract Only).

Ding, Z. et al., "A minimally invasive approach for efficient gene delivery to rodent hearts," *Gene Therapy*, (Feb. 2004), pp. 260-265, vol. 11, No. 3 (Abstract Only).

Inoue H. et al., "T-1032, a novel specific phosphodiesterase type 5 Inhibitor increases venous compliance in anesthetized rats," *Eur. J. Pharmacol.*, (Jun. 2001), pp. 109-114, vol. 422, No. 1-3 (Abstract Only).

Takagi, M. et al., "Pharmacologicla profile of T-1032, a novel specific phosphodiesterase type 5 inhibitor, in isolated rat aorta and rabbit copus cavernosum," *Eur. J. Pharmacol.*, (Jun. 2001), pp. 161-168, vol. 411, No. 1-2 (Abstract Only).

* cited by examiner

METHODS AND COMPOSITIONS FOR NUCLEIC ACID DELIVERY

This application claims the benefit of U.S. provisional application No. 60/240,231 filed on Oct. 13, 2000, the disclosure of which is incorporated herein by reference.

STATEMENT OF U.S. GOVERNMENT SUPPORT

Funding for the present invention was provided in part by the Government of the United States by virtue of the National Institutes of Health grant. Accordingly, the Government of the United States has certain rights in this invention.

BACKGROUND OF THE INVENTION

1. Field of the Invention

The present invention relates to improved gene transfer methods and, more particularly, methods that enable highly efficient and widespread delivery of selected nucleic acids, to solid organs such as the heart or liver as well as to other solid cell masses such as a solid tumor. Preferred methods of the invention include treatment of tissue and/or cells for delivery of nucleic acid with one or more phosphodiesterase inhibitor compounds such as sildenafil.

2. Background

Effective delivery of nucleic acid to cells or tissue with high levels of expression are continued goals of gene transfer technology. As a consequence of the general inability to achieve those goals to date, however, clinical use of gene transfer methods has been limited.

Thus, for example, several delivery schemes have been explored for in vivo myocardial gene transfer, but none has proven capable of modifying a majority of cardiac myocytes in a homogeneous fashion. Techniques involving injection directly into the myocardium are considered of limited use because gene expression does not extend significantly beyond the needle track. R. J. Guzman et al. *Circ Res* 1993; 73:1202–1207; A. Kass-Eisler *Proc Natl Acad Sci* 1993; 90:11498–11502. In one study, percutaneous intracoronary delivery of $10^{10}$ pfu of adenovirus caused infection in only about one-third of the myocytes in the region served by the target artery. E. Barr et al. *Gene Therapy* 1994, 1:51–58.

Other coronary delivery models, either in situ or ex vivo, have produced a very small percentage of infected cells spread throughout the heart. J. Muhlhauser et al. *Gene Therapy* 1996; 3:145–153; J. Wang et al. *Transplantation* 1996; 61:1726–1729. To date, no in vivo delivery system has been able to infect a majority of cells in an intact heart.

Certain gene delivery procedures also have been quite invasive and hence undesirable. For example, one report describes essentially complete loss of endothelium by mechanical or proteolytic means to enable gene transfer from blood vessels to cells positioned across interposing endothelial layers. See WO 93/00051.

Certain gene transfer applications also have been explored in other organs such as the liver. In particular, ex vivo strategies have included surgical removal of selected liver cells, genetic transfer to the cells in culture and then reimplantion of the transformed cells. See M. Grossman et al., *Nat Genet* 1994, 6:335–341. Such an ex vivo approach, however, suffers from a number of drawbacks including, for example, the required hepatocyte transplantation. M. A. Kay et al., *Science* 1993, 262:117–119; and S. E. Raper et al., *Cell Transplant* 1993, 2:381–400. In vivo strategies for gene transfer to the liver also have been investigated, but have suffered from low delivery efficiencies as well as low specificity to the targeted tissue. N. Ferry et al., *Proc Natl Acad Sci USA* 1991, 88:8377–8391; A. Lieber et al. *Proc Natl Acad Sci USA* 1995, 6:6230–6214; A. L. Vahrmeijer et al., *Reg Cancer Treat* 1995, 8:25–31. See also P. Heikkilia et al., *Gene Ther* 1996, 3(1):21–27.

Gene transfer has been generally unsuccessful in additional applications. For example, gene transfer therapies for treatment of cystic fibrosis have largely failed because transduction of insufficient numbers of cells.

It thus would be desirable to have improved methods and systems to effectively deliver nucleic acid to targeted cells and tissue. It would be particularly desirable to have new methods and systems for effective delivery of nucleic acids into solid organs, especially the heart, liver, lung and the like, as well as other solid cell masses such as a solid tumor.

SUMMARY OF THE INVENTION

We have now found methods and compositions that enable effective delivery of nucleic acids to desired cells, including to a solid mass of cells, particularly a solid organ such as a mammalian heart, liver, kidney, skeletal muscle, spleen or prostate, or to malignant cells such as a solid tumor. These methods and compositions enable effective gene transfer and subsequent expression of a desired gene product to a majority of cells throughout a solid cell mass, and/or gene transfer and subsequent expression of a desired gene product to a solid cell mass.

We have found that administration of one or more PDE inhibitor compounds, particularly a PDE-5 inhibitor compound such as sildenafil can significantly enhance nucleic acid delivery to targeted tissue.

Without being bound by any theory, we believe that administration of a PDE-5 inhibitor compound can amplify endogenous cGMP thereby causing an increase in vascular permeability.

We also have found particularly enhanced nucleic acid delivery results from combined administration of a PDE-5 inhibitor compound such as sildenafil and a further distinct permeability enhancement agent such as VEGF. Accordingly, such a "cocktail" of a PDE inhibitor compound and an additional, distinct permeability enhancement agent such as VEGF is particularly preferred.

Methods and compositions of the invention preferably provide enhanced vascular permeability that enables increased nucleic acid delivery to targeted cells. In particular, methods of the invention provide for treatment of treated cells with one or more phosphodiesterase inhibitor compounds. Particularly preferred permeability enhancement compounds include sildenafil, zaprinast and T-1032 (Tanabe Seiyaku Co.).

Examples of particular phosphodiesterase (PDE) inhibitors have been previously reported in U.S. Pat. Nos. 6,100,270; 6,006,735; 6,143,757; 6,143,746; 6,140,329; 6,117,881; 6,043,252; 6,001,847; 5,981,527; and 6,207,829 B1; the disclosures of which patents are incorporated herein by reference. See also PCT/EP95/04065; WO-A-93/06104; WO-A-93/07149; WO-A-93/12095; WO-A-94/00453; EP 0 463756 B1; and WO-A-94/05661 for additional compounds. See also U.S. Pat. Nos. 4,753,945; 5,010,086; 6,121,279; 6,156,753; 6,054,475; 5,091,431; 6,127,363 and 6,040,309 for additional compounds useful as nucleic acid delivery agents in accordance with the invention. Additional PDE inhibitor compounds for use in accordance with the invention are disclosed in Komas et al., *Phosphodiesterase Inhibitors* (1996) (Schudt eds.), Academic Press, San Diego, Calif.

Preferred PDE inhibitors for use with the invention include, but are not limited to, particular bicyclic heterocylic PDE inhibitors, more preferably pyrazolo[4,3-d]prymidin-7-ones, pryazolo[3,4-d]pyrimidin-4-ones, quinazolin-4-ones, purin-6-ones, pyrido[3,2-d]pyrimidin-4-ones; as well as pharmaceutically acceptable salts thereof.

A specifically preferred pyrazolo[4,3-d]prymidin-7-one is sildenfil (Viagra™), also known as 5-[2-ethoxy-5-(4-methylpiperazin-1-ylsulphonyl)phenyl]-1-methyl-3-n-propyl-1,6-dihydro-7H-pyrazolo[4,3d]pyrimidin-7-one; as well as pharmaceutically acceptable salts thereof.

As demonstrated in the example which follow, use of a PDE inhibitor compound can significantly enhances transfer of administered nucleic acid to targeted cells. A PDE inhibitor compound suitably may be administered through the vasculature of targeted tissue prior to administration of nucleic acid, and/or the PDE inhibitor compound and exogenous nucleic acid can be administered simultaneously. Preferably, the vasculature of targeted tissue is pre-treated with a PDE inhibitor agent.

In preferred aspects of the invention, a vasculature permeability agent in addition to a PDE inhibitor is administered to tissue or cells to be treated with exogenous nucleic acid. Suitable additional, distinct permeability agents include e.g. serotonin and bradykinin. Other suitable additional, distinct permeability agents will include platelet-activating factor (PAF), prostaglandin $E_1$ ($PGE_1$), histamine, vascular endothelium growth factor (VEGF), zona occludens toxin (ZOT), interleukin-2 and other plasma kinins in addition to bradykinin. Nitric oxide agonists or promoters (activators) such as nitroglycerin or nitroprusside. Additional nitric oxide synthase activators can be readily identified by known in vitro assays that detect increases in nitric oxide activity. References herein to a nitric oxide synthase activator or nitric oxide activator or other similar term refers to compounds that activate nitric oxide synthase (e.g. at least about 10%, 20%, 30%, 40% or 50% increase relative to a control) or in such an in vitro assay.

Also preferred permeability agents that can increase cyclic guanonisine 3'-monophosphate (cGMP), such as determined by a radioimmunoassay, including such assays commercially available from Amersham Pharmacia Biotech. References herein to a cGMP activator or other similar term refers to compounds that provide increased (e.g. at least 20%, 30%, 40%, or 50% increase relative to a control) in such an in vitro assay.

Other suitable vasculature permeability agents can be readily identified, e.g. simply by testing a candidate permeability agent to determine if it enhances uptake of nucleic acid by targeted tissue relative to a control tissue sample that has not been exposed to the candidate permeability agent.

A single or a combination of more than one distinct permeability agents may be administered in a particular application. In this regard, a particular application can be optimized by selection of an optimal permeability agent, or optimal "cocktail" of multiple permeability agents. Such optional agent(s) can be readily identified by those skilled in the art by routine procedures, e.g. testing selected permeability agents and combinations thereof in in vivo assays.

Low extracellular calcium ion concentration conditions also can be used to enhance vascular permeability. It has been found that transfer of administered nucleic acid to targeted cells is substantially enhanced under such conditions. Low calcium concentration conditions may be readily provided, particularly by perfusing a low calcium ion concentration fluid through the vasculature of the tissue to which nucleic acid is administered. Suitable perfusate calcium ion concentrations may be about 500 μmol/L or less, e.g. within a range from about 40 or 50 μmol/L to about 500 μmol/L, more preferably from about 50 μmol/L to about 200 μmol/L. A perfusate calcium concentration of about 50 μmol/L is particularly preferred. Calcium ion (e.g. $Ca^{2+}$) concentration also can be lowered through use of a suitable buffer such as a chelating agent, e.g. ethylenebis(oxyethylenenitrilo)tetracetic acid (EGTA), ethylenediaminetetracetic acid (EDTA), or 1,2-bis-(2-aminophenoxy)ethane-N,N,N',N'-tetraacetic acid (BAPTA).

Administration conditions in addition to those discussed above also will impact efficiency of nucleic acid uptake by targeted tissue. In particular, concentration, amount and exposure time of the administered nucleic acid and temperature of the targeted tissue all can effect the rate of gene transfer. Flow rate and perfusion pressure also can effect the rate of gene transfer.

More specifically, in a perfusion administration protocol, the rate of gene transfer increases with increase in concentration, total amount and exposure time of the administered nucleic acid in a perfusate. High concentration of nucleic acid in a perfusate especially can increase gene transfer rate. Preferred perfusate concentrations can vary with a number of factors including the particular organ or cell mass being treated, the particular cloning vehicle being administered and the like. However, in general, preferred concentrations of a viral vector in an administered perfusate are about $1 \times 10^8$ pfu/ml or greater, more preferably a concentration of about $5 \times 10^8$ pfu/ml or greater. Administered perfusate also preferably may be recirculated and readministered to a subject, e.g. to limit the total viral burden introduced into the target, or if the administered agent is in short supply. However, effective gene transfer can be achieved without recirculation, particularly if other delivery parameters are optimized. Increases in either flow rate of perfusate pressure generally will increase gene transfer efficiency, although for clinical safety it can be desirable to limit both perfusate pressure and flow rate.

The rate of gene transfer also decreases with decreased temperature of targeted tissue, particularly where the tissue is below about 20° C. Delivery of the nucleic acid near body temperature of the subject is preferred, e.g. where the nucleic acid is administered at a temperature of from about 28–45° C., more preferably from about 34–40° C. However, gene transfer can be achieved over wide temperature ranges, e.g. at about 4° C. Clinical circumstances may require lower temperatures, e.g. with gene transfer during cardiac surgery.

Nucleic acid administered in accordance with the invention can express a desired therapeutic agent, or may inhibit expression or function of an endogenous gene of a subject. Nucleic acid also may be administered for diagnostic purposes, for example to express a marker protein. In addition to such therapeutic and diagnostic methods, methods and compositions of the invention also may be employed to examine the effect of a heterologous gene on an intact organ such as a subject's heart, to create animal models of disease and to provide mechanistic information regarding various disease states.

In a preferred aspect, the invention includes methods for xenotransplantation. Thus, for example, cells of xenogeneic tissue, particularly cells of a xenogeneic solid cells mass, can be administered exogenous nucleic acid under enhanced vascular permeability as described herein. Those cells containing exogenous nucleic acid then may be transplanted into a subject. More particularly, the exogenous nucleic acid can be administered in vivo or ex vivo to donors cells or organs, e.g. a xenogeneic heart, liver, spleen and the like, in accordance with the invention and the donor cells or organ can be transplanted to a selected host, e.g. a mammal, particularly a primate such as a human. Suitable donor organs may be obtained from e.g. another primate, or a swine, particularly a pig. A variety of exogenous nucleic acids can be administered to the donor cells. For instance, nucleic acids can be administered that will express a gene product that can promote a desired phenotypic characteristic. Exemplary gene products include those which can reduce immune system recognition of the xenotransplanted cells.

In another aspect, the invention provides methods and compositions for enhancing nucleic acid delivery to targeted cells by use a vasculature permeability enhancement that is a promotes nitric oxide synthase or camp, such as nitroglycerin or nitroprusside, i.e. alone without co-administration with a PDE inhibitor compound.

In another aspect, the invention includes vasculature permeability and gene transfer solutions useful in the methods of the invention. Such solutions in general will be formulated to provide enhanced permeability to treated tissue upon administration of nucleic acid to such layers. Thus, suitable permeability agents will include one or more permeability agents as disclosed herein, particularly at least one PDE inhibitor compounds, and optionally one or more additional, distinct permeability agents, and optionally low calcium ion concentrations (e.g. about 500 µmol/L or less). A solution of the invention also may contain one or more therapeutic agents, e.g. one or more exogenous nucleic acids (e.g. one or more recombinant adenoviruses) to be administered to a subject, or other pharmaceutical agent such as nitroglycerine to control vasospasms and the like to a solution that will be administered to a heart. A permeability or gene transfer solution may suitably contain nucleic acid in a form for administration e.g. in a suitable cloning vehicle such as a viral vector dissolved in desired pharmaceutically acceptable carrier e.g. Krebs solution or other buffered solution. A permeability or gene transfer solution of the invention preferably will be pharmaceutically acceptable, e.g. sterile and otherwise suitable for administration to a subject. Typically a vasculature permeability or gene transfer solution will be stored in a sealed (preferably, hermetically sealed) container prior to use. A permeability or gene transfer solution preferably will contain active ingredients (i.e., permeability agent, calcium ion concentration, nucleic acid) in optimal dosage quantities. Solutions of the invention may suitably have other agents such as various buffers, sugars, salts and the like.

A wide variety of cells may be treated in accordance with the invention. Suitable cells for administration include those that have a distinct circulation, or circulation that can be isolated in some manner. Thus, for example, organs and other cell masses are suitable for administration in accordance with the invention including e.g. heart, lung, liver, kidney, prostrate, testes, ovaries, skeletal muscle, kidneys, brain, spleen and solid tumors. Exemplary tumors that can be treated in accordance with the invention include e.g. cancers of the lung, prostate, liver, brain, testes or ovaries. Cells treated in accordance with the invention may be in either a healthy or diseased state. A wide variety of subjects also may be treated in accordance with the invention. Typical subjects include mammals, particularly primates, especially humans.

Other aspects of the invention are discussed below.

BRIEF DESCRIPTION OF THE DRAWINGS

FIG. 2 includes FIGS. 2(a) and 2(b).

DETAILED DESCRIPTION OF THE INVENTION

Figure 1:
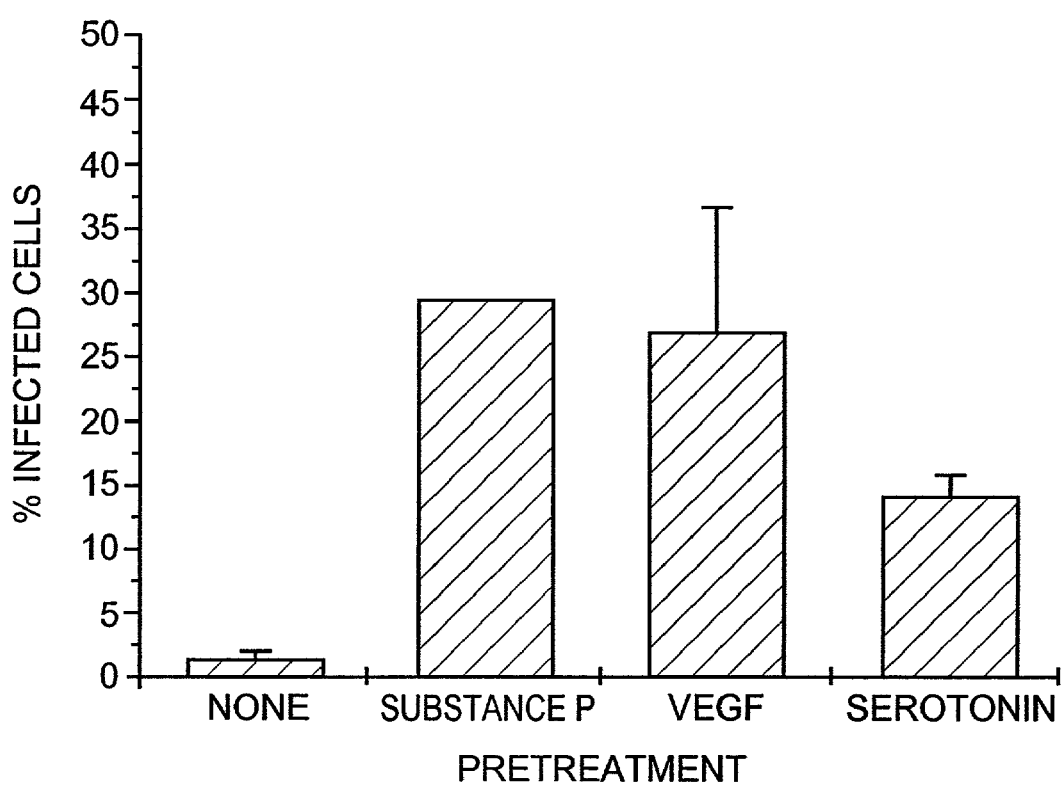
FIG. 1A shows results of Example 1, particularly enhanced gene transfer with a PDE inhibitor use (Substance P).

As stated above, the present invention provides methods and compositions that enable effective delivery of nucleic acid to desired cells, including to cells of a solid cell mass, e.g. of an organ such as a mammalian heart or liver, or other solid cell mass such as a solid tumor.

We have found that administration of one or more PDE inhibitor compounds, particularly a PDE-5 inhibitor compound such as sildenafil can significantly enhance nucleic acid delivery to targeted tissue.

In additional aspects, the invention includes methods and compositions as disclosed herein that include use or administration or inclusion of Substance P, nitroglycerin, nitroprissude (such as sodium nitroprusside), 8-Br-cGMP, zaprinast and T-1032 as the sole agent for enhancing nucleic acid delivery, or in combination with one or more other agents as disclosed herein such as sildenafil or other PDE-5 inhibitor compound, or other agent such as VEGF.

Preferably, the methods and compositions of the invention provide enhanced microvascular permeability that enables increased gene transfer to targeted cells. As discussed above, these methods and compositions create transient permeability of endothelial layers and without significant degradation or injury to endothelial cell layers of a solid cell mass.

As used herein, the term "without significant degradation or injury to endothelial cell layers" or other similar phrase means that less than 25%, more typically less than 15 or 10 percent, of endothelial cells are lost from the treated vessel wall prior to administration of nucleic acid to a subject. This contrasts from denuding and consequent injury of the endothelium through mechanical trauma or use of proteolytic enzymes which would result through use of prior methods. Lack of significant degradation of endothelial cell layers can be readily determined, e.g. by microscopic examination of the layer. Also, lack of significant degradation of endothelial cell layers can be determined by simple testing. For example, an endothelial layer can be tested to determine whether the layer has maintained a particular function and therefore is significantly degraded, e.g. a layer's ability to exhibit a reversible vasodilator response to $10^{-7}$ mol/L acetylcholine.

In addition to the above discussed PDE inhibitor compounds, suitable PDE inhibitor compounds for use in the methods of the invention are disclosed below, include compounds of the following Formulae I to XIII, which are generally preferred for use with the present invention. It should be appreciated however that the present invention is not limited by any particular PDE inhibitor compound, and the invention is applicable to any such PDE inhibitor compound now known or subsequently discovered or developed.

In general, PDE-5 inhibitor compounds are preferred for use in the methods and compositions of the invention.

More specifically, in one invention embodiment, at least one of the administered compounds is a bicyclic heterocyclic PDE inhibitor such as described in the U.S. Pat. No. 6,100,270, preferably at least one of the following pyrazolo[4,3-d]prymidin-7-ones, pryazolo[3,4-d]pyrimidin-4-ones, a quinazolin-4-ones, a purin-6-ones, or pyrido[3,2-d]pyrimidin-4-ones set forth in the following Formulae I–V including pharmaceutically acceptable salts thereof.

Suitable PDE inhibitor compounds include those of the following Formula I:

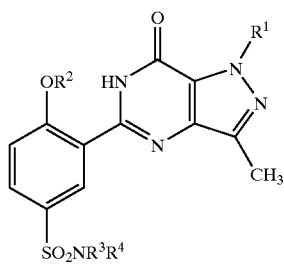

(I)

wherein in Formula I, $R^1$ is methyl or ethyl; $R^2$ is ethyl or n-propyl; and $R^3$ and $R^4$ are each independently H, or $C_1$–$C_6$ alkyl optionally substituted with $C_5$–$C_7$ cycloalkyl or with morpholino; and pharmaceutically acceptable salts thereof.

Suitable PDE inhibitor compounds also include those of the following Formula II:

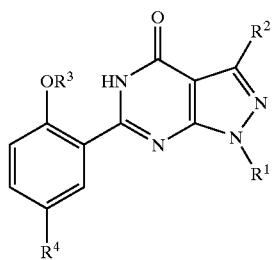

(II)

wherein in Formula II is $C_1$–$C_6$ alkyl; $R^2$ is H; methyl or ethyl;
$R^3$ is $C_2$–$C_4$ alkyl;
$R^4$ is H; $C_1$–$C_4$ alkyl optionally substituted with $NR^5R^6$, CN, $CONR^5R^6$ or $CO_2R^7$; $C_2$–$C_4$ alkenyl optionally substituted with CN, $CONR^5R^6$ or $CO_2R^7$; $C_2$–$C_4$ alkanoyl optionally substituted with $NR^5R^6$; $SO_2NR^5R^6$; $CONR^5R^6$; $CO_2R^7$ or halo;
$R^5$ and $R^6$ are each independently H or $C_1$–$C_4$ alkyl; or, together with the nitrogen atom to which they are attached, form a pyrrolidino, piperidino, morpholino, 4-($NR^8$)-1-piperazinyl or 1-imidazolyl group wherein said group is optionally substituted with one or two $C_1$–$C_4$ alkyl groups;
$R^7$ is H or $C_1$–$C_4$ alkyl;
and $R^8$ is H; $C_1$–$C_3$ alkyl or (hydroxy)$C_2$–$C_3$ alkyl; and pharmaceutically salts thereof.

Additional suitable PDE inhibitor compounds include those of the following Formula (III):

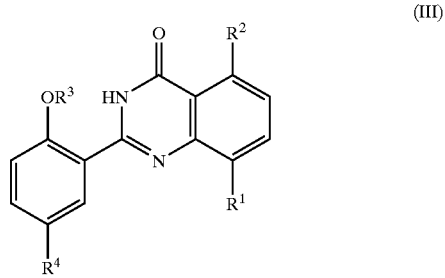

(III)

wherein in Formula III $R^1$ is H; $C_1$–$C_4$ alkyl; $C_1$–$C_4$ alkoxy or $CONR^5R^6$;
$R^2$ is H or $C_1$–$C_4$ alkyl;
$R^3$ is $C_2$–$C_4$ alkyl;
$R^4$ is H; $C_2$–$C_4$ alkanoyl optionally substituted with $NR^7R^8$; (hydroxy)$C_2$–$C_4$ alkyl optionally substituted with $NR^7R^8$; CH=CHCO$_2R^9$; CH=CHCONR$^7R^8$; $CH_2CH_2CO_2R^9$; $CH_2CH_2CONR^7R^8$; $SO_2NR^7R^8$; $SO_2NH(CH_2)_nNR^7R^8$ or imidazolyl;
$R^5$ and $R^6$ are each independently H or $C_1$–$C_4$ alkyl;
$R^7$ and $R^8$ are each independently H or $C_1$–$C_4$ alkyl; or, together with the nitrogen atom to which they are attached, form a pyrrolidino, piperidino, morpholino or 4-($NR^{10}$)-1-piperazinyl group wherein any of said groups is optionally substituted with $CONR^5R^6$;
$R^9$ is H or $C_1$–$C_4$ alkyl;
$R^{10}$ is H; $C_1$–$C_3$ alkyl or (hydroxy)$C_2$–$C_3$ alkyl;
and n is 2, 3 or 4;
with the proviso that $R^4$ is not H when $R^1$ is H, $C_1$–$C_4$ alkyl or $C_1$–$C_4$ alkoxy; and pharmaceutically acceptable salts thereof.

Suitable PDE inhibitor compounds include those of the following Formula IV:

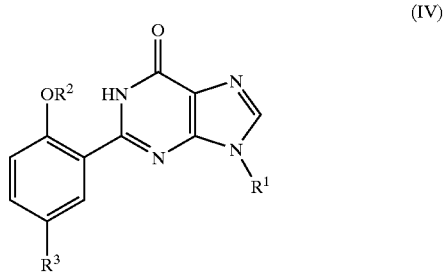

(IV)

wherein $R^1$ is $C_1$–$C_4$ alkyl; $R^2$ is $C_2$–$C_4$ alkyl;
$R^3$ is H or $SO_2NR^4R^5$;
$R^4$ and $R^5$ together with the nitrogen atom to which they are attached form a pyrrolidino, piperidino, morpholino or 4-($NR^6$)-1-piperazinyl group;
and $R^6$ is H or $C_1$–$C_3$ alkyl; and pharmaceutically acceptable salts thereof.

Additional suitable PDE inhibitor compounds include those of the following Formula (V):

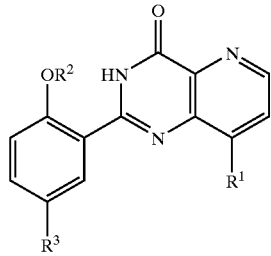

wherein in Formula V $R^1$ is H; $C_1$–$C_4$ alkyl; CN or $CONR^4R^5$; $R^2$ is $C_2$–$C_4$ alkyl;
$R^3$ is $SO_2NR^6R^7$; $NO_2$; $NH_2$; $NHCOR^8$; $NHSO_2R^8$ or $N(SO_2R^8)_2$;
$R^4$ and $R^5$ are each independently selected from H and $C_1$–$C_4$ alkyl;
$R^6$ and $R^7$ are each independently selected from H and $C_1$–$C_4$ alkyl optionally substituted with $CO_2R^9$, OH, pyridyl, 5-isoxazolin-3-onyl, morpholino or 1-imidazolidin-2-onyl; or, together with the nitrogen atom to which they are attached, form a pyrrolidino, piperidino, morpholino, 1-pyrazolyl or 4-($NR^{10}$)-1-piperazinyl group wherein any of said groups may optionally be substituted with one or two substituents selected from $C_1$–$C_4$ alkyl, $CO_2R^9$, $NH_2$ and OH;
$R^8$ is $C_1$–$C_4$ alkyl or pyridyl;
$R^9$ is H or $C_1$–$C_4$ alkyl;
and $R^{10}$ is H; $C_1$–$C_4$ alkyl or (hydroxy)$C_2$–$C_3$ alkyl; and a pharmaceutically acceptable salt thereof A preferred group of compounds of Formula I above include those wherein:
$R^3$ is H; methyl or ethyl;
$R^4$ is $C_1$–$C_6$ alkyl optionally substituted with cyclohexyl or with morpholino; and
$R^1$ and $R^2$ are as previously defined for formula (I), and pharmaceutically acceptable salts thereof.

Preferred compounds of Formula II above include those wherein $R^1$ is n-propyl; $R^2$ is H or methyl; $R^3$ is ethyl or n-propyl; $R^4$ is H; ethyl substituted with $CONR^5R^6$ or $CO_2R^7$; vinyl substituted with $CONR^5R^6$ or $CO_2R^7$; acetyl substituted with $NR^5R^6$; $SO_2NR^5R^6$; $CONR^5R^6$; $CO_2R^7$ or bromo; $R^5$ and $R^6$ together nitrogen atom to which they are attached form a morpholino, 4-($NR^8$)-1-piperazinyl or 2,4-dimethyl-1-imidazolyl group; $R^7$ is H or t-butyl; and $R^8$ is methyl or 2-hydroxyethyl; and pharmaceutically acceptable salts thereof.

Preferred compounds of Formula III above include those where $R^1$ is H; methyl; methoxy or $CONR^5R^6$; $R^2$ is H or methyl; $R^3$ is ethyl or n-propyl; $R^4$ is H; acetyl optionally substituted with $NR^7R^8$; hydroxyethyl substituted with $NR^7R^8$; CH=$CHCO_2R^9$; CH=$CHCONR^7R^8$; $CH_2CH_2CO_2R^9$; $SO_2NR^7R^8$; $SO_2NH(CH_2)_3NR^7R^8$ or 1-imidazolyl; $R^5$ and $R^6$ are each independently H or ethyl; $R^7$ and $R^8$ together with the nitrogen atom to which they are attached form a piperidino, 4-carbamoylpiperidino, morpholino or 4-($NR^{10}$)-1-piperazinyl group; $R^9$ is H or t-butyl; and $R^{10}$ is H; methyl or 2-hydroxyethyl; with the proviso that $R^4$ is not H when $R^1$ is H, methyl or methoxy; and pharmaceutically acceptable salts thereof.

Preferred compounds of Formula IV above include those wherein $R^1$ and $R^2$ are each independently ethyl or n-propyl; $R^4$ and $R^5$ together with the nitrogen atom to which they are attached form a 4-($NR^6$)-1-piperazinyl group; and $R^3$ and $R^6$ are as previously defined for Formula IV; and pharmaceutically acceptable salts thereof.

Preferred compounds of Formula V above include compounds wherein $R^1$ is H; n-propyl; CN or $CONH_2$; $R^2$ is ethyl; $R^3$ is $SO_2NR_6R^7$; $NO_2$; $NH_2$; $NHCOCH(CH_3)_2$; $NHSO_2CH(CH_3)_2$; $NHSO_2$(3-pyridyl) or $N[SO_2(3-pyridyl)]_2$; $R^6$ is H; methyl or 2-hydroxyethyl; $R^7$ is methyl optionally substituted with 2-pyridyl or 5-isoxazolin-3-onyl; or ethyl 2-substituted with OH, $CO_2CH_2CH_3$, morpholino or 1-imidazolidin-2-onyl; or $R^6$ and $R^7$ together with the nitrogen atom to which they are attached form a (4-$CO_2R^9$) piperidino, 5-amino-3-hydroxy-1-pyrazolyl or 4-($NR^{10}$)-1-piperazinyl group; $R^9$ is H or ethyl; and $R^{10}$ is H; methyl or 2-hydroxyethyl.

A particularly preferred group of compounds is that of Formula III above wherein $R^1$ is methyl; $CONH_2$ or $CONHCH_2CH_3$; $R^2$ is H; $R^3$ is ethyl or n-propyl; $R^4$ is H; acetyl; 1-hydroxy-2-($NR^7R^8$)ethyl; CH=$CHCO_2C(CH_3)_3$; CH=$CHCONR^7R^8$; $SO_2NR^7R^8$ or 1-imidazolyl, $R^7$ and $R^8$ together with the nitrogen atom to which they are attached form a 4-($NR^{10}$)-1-piperazinyl group; and $R^{10}$ is methyl or 2-hydroxyethyl; with the proviso that $R^4$ is not H when $R^1$ is methyl; of formula (IV) wherein $R^1$ is n-propyl; $R^2$ is ethyl; and $R^3$ is 1-piperazinylsulphonyl or 4-methyl-1-piperazinylsulphonyl; and of formula (V) wherein $R^1$ is n-propyl or CN; $R^2$ is ethyl; $R^3$ is $SO_2NR^6R^7$; $NHSO_2CH(CH_3)_2$; $NHSO_2$(3-pyridyl) or $N[SO_2(3-pyridyl)]_2$; $R^6$ is H or methyl; $R^7$ is methyl; or ethyl 2-substituted with $CO_2CH_2CH_3$; morpholino or 1-imidazolidin-2-onyl; or $R^6$ and $R^7$ together with the nitrogen atom to which they are attached form a (4-$CO_2R^9$)piperidino or 4-($NR^{10}$)-1-piperazinyl group; $R^9$ is H or ethyl; and $R^{10}$ is H; methyl or 2-hydroxyethyl.

Especially preferred individual compounds of the invention include:
1-ethyl-5-[5-(n-hexylsulphamoyl)-2-n-propoxy-phenyl]-3-methyl-1,6-dihydro-7H-pyrazolo[4,3-d]pyrimidin-7-one;
1-ethyl-5-(5-diethylsulphamoyl-2-n-propoxy-phenyl)-3-methyl-1,6-dihydro-7H-pyrazolo[4,3-d]-pyrimidin-7-one;
5-[5-(N-cyclohexylmethyl-N-methylsulphamoyl)-2-n-propoxyphenyl]-1-ethyl-3-methyl-1,6-dihydro-7H-pyrazolo[4,3-d]pyrimidin-7-one;
6-(5-bromo-2-n-propoxyphenyl)-3-methyl-1-n-propyl-1,5-dihydro-4H-pyrazolo[3,4-d]pyrimidin-4-one;
3-methyl-6-(5-morpholinosulphonyl-2-n-propoxyphenyl)-1-n-propyl-1,5-dihydro-4H-pyrazolo[3,4-d]pyrimidin-4-one;
6-[5-(2-carboxyvinyl)-2-n-propoxzphenyl]-3-methyl-1-n-propyl-1,5-dihydro-4H-pyrazolo[3,4-d]pyrimidin-4-one;
6-[5-(2-t-butoxycarbonylvinvy)-2-n-propoxyphenyl]-3-methyl-1-n-propyl-1,5-dihydro-4H-pyrazolo[3,4-d]pyrimidin-4-one;
3-methyl-6-[5-(2-morpholinocarbonylvinyl)-2-n-propoxyphenyl]-1-n-propyl-1,5-dihydro-4H-pyrazolo[3,4-d]pyrimidin-4-one;
3-methyl-6-[5-(2-morpholinocarbonylethyl)-2-n-propoxyphenyl]-1-n-propyl-1,5-dihydro-4H-pyrazolo[3,4-d]pyrimidin-4-one;
2-{2-ethoxy-5-[4-(2-hydroxyethyl)-1-piperazinyl-sulphonyl]phenyl}-8-methylquinazolin-4-(3H)-one;
2-{5-[4-(2-hydroxyethyl)-1-piperazinylsulphonyl]-2-n-propoxyphenyl}-8-methylquinazolin-4(3H)-one;

8-methyl-2-{5-[2-(4-methyl-1-piperazinylcarbonyl)-ethenyl]-2-n-propoxyphenyl}quinazolin-4(3H)-one;

8-carbamoyl-2-{2-ethoxy-5-[4-(2-hydroxyethyl)-1-piperazinylsulphonyl]phenyl}quinazolin-4(3H)-one;

8-ethylcarbamoyl-2-(2-n-propoxyphenyl)quinazolin-4(3H)-one;

2-[2-ethoxy-5-(4-ethoxycarbonylpiperidino-sulphonyl)phenyl]-8-n-propylpyrido[3,2-d]pyrimidin-4(3H)-one;

2-[5-(4-carboxypiperidinosulphonyl)-2-ethoxyphenyl]-8-n-propylpyrido[3,2-d]pyrimidin-4(3H)-one;

2-{2-ethoxy-5-[4-(2-hydroxyethyl)-1-piperazinyl-sulphonyl]phenyl}-8-n-propylpyrido[3,2-d]pyrimidin-4(3H)-one;

and 2-{2-ethoxy-5-[(bis-3-pyridylsulphonyl)amino]-phenyl}-8-n-propylpyrido[3,2-d]pyrimidin-4(3H)-one.

In another invention embodiment, at least one of the administered compounds is a tetracyclic cGMP specific PDE inhibitor such as those described in U.S. Pat. No. 6,143,746 and as set forth in the following Formulae VI–IX including pharmaceutically acceptable salts thereof.

Mores specifically, suitable compounds include those of the following Formula VI:

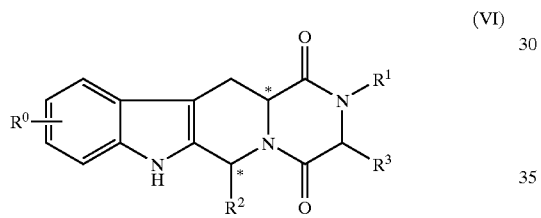

(VI)

wherein in Formula VI $R^0$ represents hydrogen, halogen, or $C_{1-6}$ alkyl;

$R^1$ represents hydrogen, $C_{1-6}$ alkyl, $C_{2-6}$ alkenyl, $C_{2-6}$ alkynyl, halo$C_{1-6}$ alkyl, $C_{3-8}$ cycloalkyl, $C_{3-8}$ cycloalkyl$C_{1-3}$ alkyl, aryl$C_{1-3}$ alkyl, or heteroaryl$C_{1-3}$ alkyl;

$R^2$ represents an optionally substituted monocyclic aromatic ring selected from benzene, thiophene, furan, and pyridine, or an optionally substituted bicyclic ring;

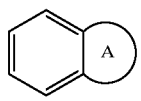

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur, and nitrogen; and $R^3$ represents hydrogen of $C_{1-3}$ alkyl, or $R^1$ and $R^3$ together represent a 3- or 4-membered alkyl or alkenyl chain; and pharmaceutically and salts and solvates (e.g., hydrates) thereof.

Suitable compounds also include those of the following Formula VII:

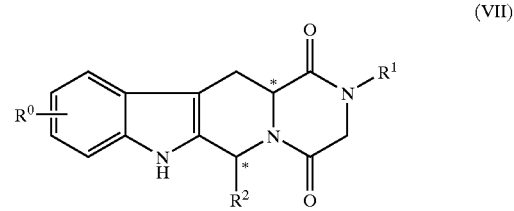

(VII)

wherein in Formula VII $R^0$ represents hydrogen, halogen, or $C_{1-6}$ alkyl;

$R^1$ represents hydrogen, $C_{1-6}$ alkyl, halo$C_{1-6}$ alkyl, $C_38$ cycloalkyl$C_{1-3}$ alkyl, aryl$C_{1-3}$ alkyl, or heteroaryl$C_{1-3}$ alkyl; and $R^2$ represents an optionally substituted monocyclic aromatic ring selected from benzene, thiophene, furan, and pyridine, or an optionally substituted bicyclic ring

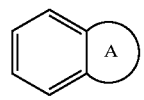

attached to the rest of the molecule via one of the benzene ring carbon atoms, and wherein the fused ring A is a 5- or 6-membered ring which can be saturated or partially or fully unsaturated and comprises carbon atoms and optionally one or two heteroatoms selected from oxygen, sulphur, and nitrogen; and pharmaceutically acceptable salts and solvates (e.g., hydrates) thereof.

A further subgroup of compounds of Formula VI preferred for use in the methods of the invention, are compounds of the following Formula VIII:

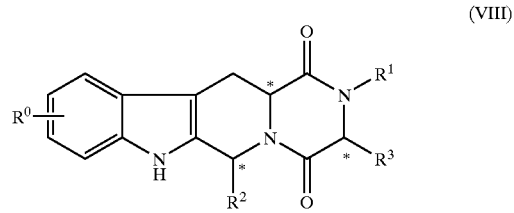

(VIII)

wherein in Formula VIII:
$R^0$ represents hydrogen, halogen, or $C_{1-6}$ alkyl;
$R^1$ represents hydrogen or $C_{1-6}$ alkyl;
$R^2$ represents the bicyclic ring

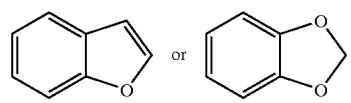

which can be optionally substituted by one or more groups selected from halogen and $C_{1-3}$ alkyl; and $R^3$ represents hydrogen or $C_{1-3}$ alkyl; and pharmaceutically acceptable salts and solvates (e.g., hydrates) thereof.

In Formula VII above, with respect to $R^1$, the term "aryl" as part of an aryl$C_{1-3}$ alkyl group means phenyl or phenyl substituted by one or more (e.g., 1, 2, or 3) substituents selected from halogen, $C_{1-6}$ alkyl, $C_{1-6}$ alkoxy, and methylenedioxy. The term "heteroaryl" as part of a heteroaryl$C_{1-3}$ alkyl group means thienyl, furyl, or pyridyl, each optionally substituted by one or more (e.g., 1, 2, or 3) substituents selected from halogen, $C_{1-6}$ alkyl, and $C_{1-6}$ alkoxy. The term "$C_{3-8}$ cycloalkyl" as a group or part of a $C_{3-8}$ cycloalkyl$C_{1-3}$ alkyl group means a monocyclic ring comprising three to eight carbon atoms. Examples of suitable cycloalkyl rings include the $C_{3-6}$ cycloalkyl rings cyclopropyl, cyclobutyl, cyclopentyl, and cyclohexyl.

In formula VII above, with respect to $R^2$, optional benzene ring substituents are selected from one or more (e.g., 1, 2, or 3) atoms or groups comprising halogen, hydroxy, $C_{1-6}$ alkyl, $C_{1-6}$ alkoxy, $CO_2R^b$, halo$C_{1-6}$ alkyl, halo$C_{1-6}$ alkoxy, cyano, nitro, and $NR^aR^b$, where $R^a$ and $R^b$ are each hydrogen or $C_{1-6}$ alkyl or $R^a$ also can represent $C_{2-7}$ alkanoyl or $C_{1-6}$ alkylsulphonyl. Optional substituents for the remaining ring systems are selected from one or more (e.g., 1, 2, or 3 atoms or groups comprising halogen, $C_{1-6}$ alkyl, $C_{1-6}$ alkoxy, and aryl$C_{1-3}$ alkyl as defined above. The bicyclic ring

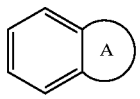

can, for example, represent naphthalene, a heterocycle such as benzoxazole, benzothiazole, benzisoxazole, benzimidazole, quinoline, indole, benzothiophene, benzofuran, or

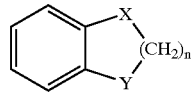

wherein n is an integer 1 or 2 and X and Y each can represent $CH_2$, O, S, or NH.

Unless otherwise indicated, in the above formulae, as well as other formulae described herein, the term "alkyl," as a group or part of a group, means a straight chain or, where available, a branched chain moiety containing the indicated number of carbon atoms. For example, it can represent a $C_{1-4}$ alkyl function as represented by methyl, ethyl, n-propyl, i-propyl, n-butyl, s-butyl, and t-butyl. The term "alkenyl" as used herein includes straight chained and branched alkenyl groups containing the indicated number of carbon atoms, such as vinyl and allyl groups. The term "alkynyl" as used herein includes straight chained and branched alkynyl groups containing the indicated number of carbon atoms, suitably acetylene.

Unless other indicated, in the above formulae, as well as other formulae disclosed herein, the term "halogen" herein means a fluorine, chlorine, bromine, or iodine atom.

Unless other indicated, in the above formulae, as well as other formulae disclosed herein, the term "halo$C_{1-6}$ alkyl" means an alkyl group as defined above comprising one to six carbon atoms substituted at one or more carbon atoms by one or more (e.g., 1, 2, or 3) halogen atoms. Similarly, a halo$C_{1-6}$ alkoxy group is a halo$C_{1-6}$ alkyl group as defined above linked to the $R^2$ benzene ring via an oxygen atom. Examples of halo $C_{1-6}$ alkyl groups include trifluoromethyl and 2,2,2-trifluoroethyl. An example of a halo$C_{1-6}$ alkoxy group is trifluoromethoxy. The term "$C_{2-7}$ alkanoyl" means a $C_{1-6}$ alkanoyl group where the $C_{1-6}$ alkyl portion is as defined above. An example of a suitable $C_{2-7}$ alkanoyl group is the $C_2$ alkanoyl group acetyl.

Unless other indicated, in the above formulae, as well as other formulae disclosed herein, when $R^0$ is a halogen atom or a $C_{1-6}$ alkyl group, this substituent can be sited at any available position on the phenyl portion of the tetracyclic ring. However, a particular site of attachment is the ring 10-position.

The compounds of Formula VI can contain two or more asymmetric centers, and, thus, can exist as enantiomers or diastereoisomers. In particular, in Formula VII above, two ring chiral centers are denoted with asterisks. It is to be understood that the invention includes both mixture and separate individual isomers of the compounds of Formula (VII).

The compounds of Formula VI also can exist in tautomeric forms, and the invention includes both mixtures and separate individual tautomers thereof.

A particular group of compounds for use in the methods of the invention are those compounds of Formula VI in which $R^0$ is hydrogen or halogen (e.g., fluorine), especially hydrogen.

Another particular group of compounds for use in the methods of the invention are those of Formula VI in which $R^1$ represents hydrogen, $C_{1-4}$ alkyl, halo$C_{1-4}$ alkyl, $C_{3-6}$ cycloalkyl, $C_{3-6}$ cycloalkylmethyl, pyridyl$C_{1-3}$ alkyl, furyl$C_{1-3}$ alkyl, or optionally substituted benzyl. Within this particular group of compounds, examples of $C_{1-4}$ alkyl groups are methyl, ethyl, n-propyl, i-propyl, and n-butyl. Examples of $C_{3-6}$ cycloalkylmethyl groups are cyclopropylmethyl and cyclohexylmethyl. Examples of optionally substituted, benzyl groups include benzyl and halobenzyl (e.g., fluorobenzyl).

A further group of compounds for use in the methods of the invention are those compounds of Formula VI in which $R^2$ represents an optionally substituted benzene, thiophene, furan, pyridine, or naphthalene ring, or an optionally substituted bicyclic ring

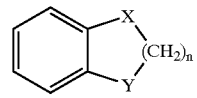

wherein n is 1 or 2, and X and Y are each $CH_2$ or O. Within this particular group of compounds, examples of substituted benzene groups are benzene substituted by one of halogen (e.g., chlorine), hydroxy, $C_{1-3}$ alkyl (e.g., methyl, ethyl, or i-propyl), $C_{1-3}$ alkoxy (e.g., methoxy or ethoxy), $CO_2R^b$, halomethyl (e.g., trifluoromethyl), halomethoxy (e.g., trifluoromethoxy), cyano, nitro, or $NR^aR^b$ wherein $R^a$ and $R^b$ are each hydrogen or methyl, or $R^a$ is acetyl, or benzene substituted by dihalo (e.g., dichloro) or by $C_{1-3}$ alkoxy (e.g., methoxy) and one of halogen (e.g., chlorine) and hydroxy. An example of a substituted thiophene ring is a halo (e.g., bromo) substituted thiophene ring.

A still further particular group of compounds of Formula VI are those where $R^3$ represents hydrogen or $R^1$ and $R^3$ together represent a 3-membered alkyl chain.

A preferred group of compounds of the invention are the cis isomers of Formula VI represented by formula (IX)

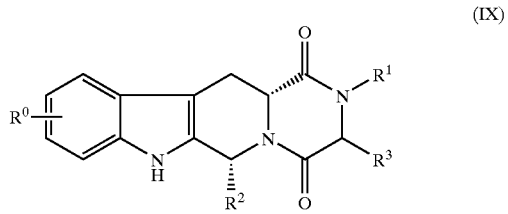

(IX)

and mixtures thereof with their cis optical enantiomers, including racemic mixtures, and salts and solvates (e.g., hydrates) of these compounds in which $R^0$ is hydrogen or halogen (e.g., fluorine), especially hydrogen, and $R^1$, $R^2$, and $R^3$ are as defined previously.

The single isomers represented by Formula IX, i.e., the 6R, 12aR isomers, are particularly preferred.

Within the above definitions for Formula IX, $R^1$ preferably can represent $C_{1-4}$ alkyl (e.g., methyl, ethyl, i-propyl, and n-butyl), $C_{3-6}$ cycloalkyl (e.g., cyclopentyl) or $C_{3-6}$ cycloalkylmethyl (e.g., cyclopropylmethyl).

$R^2$ preferably can represent a substituted benzene ring such as benzene substituted by $C_{1-3}$ alkoxy (e.g., methoxy) or by $C_{1-3}$ alkoxy (e.g., methoxy) and halogen (e.g., chlorine), particularly 4-methoxyphenyl or 3-chloro-4-methoxyphenyl, or $R^2$ preferably can represent 3,4-methylenedioxyphenyl.

A particularly preferred subgroup of compounds of the above formula are compounds wherein $R^0$ represents hydrogen.

A further preferred subgroup includes compounds wherein $R^1$ is selected from hydrogen, methyl, and isopropyl.

Preferably, $R^2$ represents the unsubstituted bicyclic ring

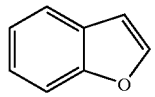

A still further subgroup of compounds of Formula IX, are compounds wherein $R^3$ represents hydrogen or methyl.

It is to be understood that the present invention covers all appropriate combinations of particular and preferred groupings hereinabove.

Particular compounds suitable for use in the methods of the invention include:
cis-2,3,6,7,12,12a-hexahydro-2-(4-pyridyl-methyl)-6-(3,4-methylenedioxyphenyl)-pyrazino[2',1';6,1]-pyrido[3,4-b]indole-1,4-dione;
cis-2,3,6,7,12,12a-hexahydro-6-(2,3-dihydrobenzo[b]furan-5-yl)-2-methylpyrazino[2',1';6,1]pyrido-[3,4-b]indole-1,4-dione;
cis-2,3,6,7,12,12a-hexahydro-6-(5-bromo-2-thienyl)-2-methylpyrazino[2',1';6,1]pyrido[3,4-b]indole-1,4-dione;
cis-2,3,6,7,12,12a-hexahydro-2-butyl-6-(4-methylphenyl)-pyrazino[2',1';6,1]pyrido[3,4-b]indole-1,4-dione;
(6R,12aR)-2,3,6,7,12,12a-hexahydro-2-isopropyl-6-(3,4-methylenedioxyphenyl)-pyrazino[2',1';6,1]pyrido-[3,4-b]indole-1,4-dione;
(6R,12aR)-2,3,6,7,12,12a-hexahydro-2-cyclopentyl-6-(3,4-methylenedioxyphenyl)-pyrazino[2',1';6,1]-pyrido[3,4-b]indole-1,4-dione;
(6R,12aR)-2,3,6,7,12,12a-hexahydro-2-cyclopropylmethyl-6-(4-methoxyphenyl)-pyrazino[2',1';6,1]-pyrido[3,4-b]indole-1,4-dione;
(6R,12aR)-2,3,6,7,12,12a-hexahydro-6-(3-chloro-4-methoxyphenyl)-2-methylpyrazino[2',1';6,1]pyrido[3,4-b]indole-1,4-dione;
(6R,12aR)-2,3,6,7,12,12a-hexahydro-2-methyl-6-(3,4-methylenedioxyphenyl)-pyrazino[2',1';6,1]pyrido[3,4-b]indole-1,4-dione;
(6R,12aR)-2,3,6,7,12,12a-hexahydro-6-(3,4-methylenedioxyphenyl)-pyrazino[2',1';6,1]pyrido[3,4-b]indole-1,4-dione;
(5aR,12R,14aS)-1,2,3,5,6,11,12,14a-octahydro-12-(3,4-methylenedioxyphenyl)-pyrrolo[1'',2'':4'5'']-pyrazino[2',1';6,1]pyrido[3,4-b]indole-5-1,4-dione;
(6R,12aR)-2,3,6,7,12,12a-hexahydro-6-(5-benzofuranyl)-2-methylpyrazino[2',1';6,1]pyrido[3,4-b]indole-1,4-dione;
(6R,12aR)-2,3,6,7,12,12a-hexahydro-6-(5-benzofuranyl)-pyrazino[2',1';6,1]pyrido[3,4-b]indole-1,4-dione;
(3S,6R,12aR)-2,3,6,7,12,12a-hexahydro-6-(5-benzofuranyl)-3-methyl-pyrazino[2',1';6,1]pyrido[3,4-b]indole-1,4-dione;
(3S,6R,12aR)-2,3,6,7,12,12a-hexahydro-6-(5-benzofuranyl)-2,3-dimethylpyrazino[2',1';6,1]pyrido[3,4-b]indole-1,4-dione;
(6R,12aR)-2,3,6,7,12,12a-hexahydro-6-(5-benzofuranyl)-2-isopropyl-pyrazino[2',1';6,1]pyrido[3,4-b]indole-1,4-dione; and physiologically acceptable solvates (e.g., hydrates) thereof.

The invention is also compatible with administration of particular cGMP PDE inhibitors disclosed in U.S. Pat. No. 6,140,329, at least some of which compounds have been described in said U.S. Pat. No. 6,143,746. Preferred compounds of the U.S. Pat. No. 6,140,329 are set forth in the following Formula X including pharmaceutically acceptable salts thereof.

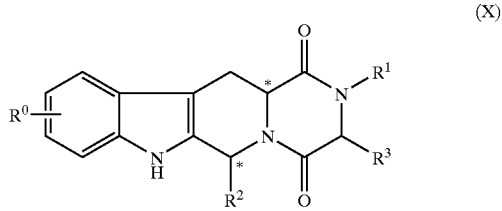

(X)

wherein in Formula X:
$R^0$ represents hydrogen, halogen or $C_{1-6}$ alkyl;
$R^1$ represents hydrogen, $C_{1-6}$ alkyl, $C_{2-6}$ alkenyl, $C_{2-6}$ alkynyl, halo$C_{1-6}$ alkyl, $C_{3-8}$ cycloalkyl, $C_{3-8}$ cycloalkyl$C_{1-3}$ alkyl, aryl$C_{1-3}$ alkyl or heteroaryl$C_{1-3}$ alkyl;
$R^2$ represents an optionally substituted monocyclic aromatic ring selected from benzene, thiophene, furan and pyridine or an optionally substituted bicyclic ring

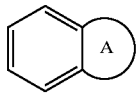

attached to the rest of the molecule via one of the benzene ring carbon atoms and wherein the fused ring A is a 5- or 6-membered ring which may be saturated or partially or fully unsaturated and comprises carbon atoms and optionally one or two heteroatoms selected from oxygen, sulphur and nitrogen; and $R^3$ represents hydrogen or $C_{1-3}$ alkyl, or $R^1$ and $R^3$ together represent a 3- or 4-membered alkyl or alkenyl chain; and pharmaceutically acceptable salts and solvates (e.g. hydrates) thereof.

Additional suitable individual compounds of the invention for use in the treatment include:

Cis-2,3,6,7,12,12a-hexahydro-2-(4-pyridylmethyl)-6-(3,4-methylenedioxyphenyl)-pyrazino[2',1':6,1]pyrido[3,4-b]indole-1,4-dione;

Cis-2,3,6,7,12,12a-hexahydro-6-(2,3-dihydrobenzo[b]furan-5-yl)-2-methylpyrazino[2',1':6,1]pyrido[3,4-b]indole-1,4-dione;

Cis-2,3,6,7,12,12a-hexahydro-6-(5-bromo-2-thienyl)-2-methylpyrazino[2',1':6,1]pyrido[3,4-b]indole-1,4-dione;

Cis-2,3,6,7,12,12a-hexahydro-2-butyl-6-(4-methylphenyl)-pyrazino[2',1':6,1]pyrido[3,4-b]indole-1,4-dione;

(6R,12aR)-2,3,6,7,12,12a-Hexahydro-2-isopropyl-6-(3,4-methylenedioxyphenyl)-pyrazino[2',1':6,1]pyrido[3,4-b]indole-1,4-dione;

(6R,12aR)-2,3,6,7,12,12a-Hexahydro-2-cyclopentyl-6-(3,4-methylenedioxyphenyl)-pyrazino[2',1':6,1]pyrido[3,4-b]indole-1,4-dione;

(6R,12aR)-2,3,6,7,12,12a-Hexahydro-2-cyclopropylmethyl-6-(4-methoxyphenyl)-pyrazino[2',1':6,1]pyrido[3,4-b]indole-1,4-dione;

(6R,12aR)-2,3,6,7,12,12a-Hexahydro-6-(3-chloro-4-methoxyphenyl)-2-methylpyrazino[2',1':6,1]pyrido[3,4-b]indole-1,4-dione;

(6R,12aR)-2,3,6,7,12,12a-Hexahydro-2-methyl-6-(3,4-methylenedioxyphenyl)-pyrazino[2',1':6,1]pyrido[3,4-b]indole-1,4-dione;

(6R,12aR)-2,3,6,7,12,12a-Hexahydro-6-(3,4-methylenedioxyphenyl)-pyrazino[2',1':6,1]pyrido[3,4-b]indole-1,4-dione;

(5aR,12R,14aS)-1,2,3,5,6,11,12,14a-Octahydro-12-(3,4-methylenedioxyphenyl)-pyrrolo[1",2":4',5']pyrazino[2',1':6,1]pyrido[3,4-b]indole-5-1,4-dione;

Cis-2,3,6,7,12,12a-hexahydro-2-cyclopropyl-6-(3,4-methylenedioxyphenyl)-pyrazino[2',1':6,1]pyrido[3,4-b]indole-1,4-dione;

(3S,6R,12aR)-2,3,6,7,12,12a-hexahydro-3-methyl-6-(3,4-methylenedioxyphenyl)-pyrazino[2',1':6,1]pyrido[3,4-b]indole-1,4-dione;

and physiologically acceptable salts and solvates (e.g. hydrates) thereof.

Specifically suitable compounds for use in the methods of the invention include:

(6R,12aR)-2,3,6,7,12,12a-hexahydro-2-methyl-6-(3,4-methylenedioxyphenyl)-pyrazino[2',1':6,1]pyrido[3,4-b]indole-1,4-dione(Compound A); and (3S,6R,12aR)-2,3,6,7,12,12a-hexahydro-2,3-dimethyl-6-(3,4-methylenedioxyphenyl)-pyrazino[2',1':6,1]pyrido[3,4-b]indole-1,4-dione (Compound B);

and physiologically acceptable salts and solvates (e.g. hydrates) thereof.

In another invention embodiment, at least one of the administered compounds is a carboline derivative or N-cinnamoyl derivative or (β) carbolines as described in the U.S. Pat. Nos. 6,043,252 and 6,117,881. Such preferred compounds are set forth in the following Formulae XI and XIII including pharmaceutically acceptable salts thereof.

Compounds of Formula XI are represented by the following structure:

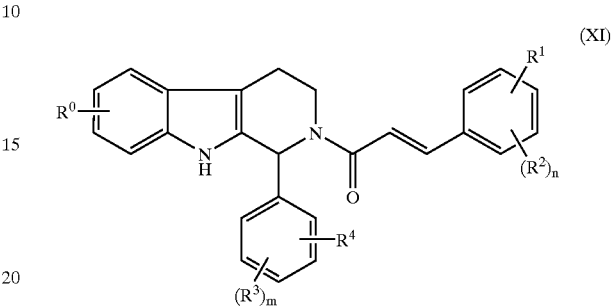

(XI)

wherein in that Formula XI:

$R^0$ represents hydrogen or halogen;

$R^1$ is selected from the group consisting of:

hydrogen, $NO_2$, trifluoromethyl, trifluoromethoxy, halogen, cyano, a 5- or 6-membered heterocyclic group containing at least one heteroatom selected from oxygen, nitrogen and sulphur, and is optionally substituted by —C(=O)$OR^a$ or $C_{1-4}$ alkyl, $C_{1-6}$ alkyl optionally substituted by —$OR^a$, $C_{1-3}$ alkoxy, C(=O)$R^a$, O—C(=O)$R^a$, C(=O)$OR^a$, $C_{1-4}$ alkyleneC(=O)$OR^a$, O—$C_{1-4}$ alkylene-C(=O)$OR^a$, $C_{1-4}$ alkylene-O—$C_{1-4}$ alkylene-C(=O)$OR^a$, C(=O)$NR^aSO_2R^c$, C(=O)$C_{1-4}$ alkyleneHet, $C_{1-4}$ alkylene$NR^aR^b$, $C_{2-6}$ alkyleneN$R^aR^b$, C(=O)$NR^aR^b$, C(=O)$NR^aR^c$, C(=O)$NR^aC_{1-4}$ alkyleneOR$^b$C(=O)$NR^aC_{1-4}$ alkyleneHet, O$R^a$O$C_{2-4}$ alkylene $NR^aR^b$, O$C_{1-4}$ alkylene-CH(O$R^a$)CH$_2$N$R^aR^b$, O—$C_{1-4}$ alkylene Het, O—$C_{2-4}$ alkylene-O$R^a$, O—$C_{2-4}$ alkylene-N$R^a$—C(=O)O$R_b$, N$R^aR^b$, N$R^aC_{1-4}$ alkyleneN$R^aR^b$, N$R^aC$(=O)$R^b$, N$R^aC$(=O) N$R^aR^b$, N(SO$_2C_{1-4}$ alkyl)$_2$, N$R^a$(SO$_2C_{1-4}$ alkyl), SO$_2NR^aR^b$, and OSO$_2$ trifluoromethyl; $R^2$ is selected from the group consisting of: hydrogen, halogen, O$R^a$, $C_{1-6}$ alkyl, NO$_2$, and N$R^aR^b$, or $R^1$ and $R^2$ are taken together to form a 3- or 4-membered alkylene or alkenylene chain component of a 5- or 6-membered ring, optionally containing at least one heteroatom;

$R^3$ is selected from the group consisting of: hydrogen, halogen, NO$_2$, trifluoromethoxy, $C_{1-6}$ alkyl, and C(=O)O$R^a$; $R^4$ is hydrogen, or $R^3$ and $R^4$ are taken together to form a 3- or 4-membered alkylene or alkenylene chain component of a 5- or 6-membered ring, optionally containing at least one heteroatom;

Het represents a 5- or 6-membered heterocyclic group containing at least one heteroatom selected from the group consisting of oxygen, nitrogen, and sulfur, and is optionally substituted with $C_{1-4}$ alkyl;

$R^a$ and $R^b$ can be the same or different, and are independently selected from hydrogen and $C_{1-6}$ alkyl;

$R^c$ represents phenyl or $C_{4-6}$ cycloalkyl, wherein the phenyl or $C_{4-6}$ cycloalkyl can be optionally substituted by one or more halogen atoms, one or more —C(=O)O$R^a$, or one or more —O$R^a$;

n is an integer selected from 1, 2 and 3;
m is an integer selected from 1 and 2;

and pharmaceutically acceptable salts and solvates (e.g., hydrates) thereof.

In the above Formula XI, the term alkyl or alkylene as used herein respectively contains the indicated number of carbon atoms and includes straight chained and branched alkyl or alkylene groups, typically methyl, methylene, ethyl, and ethylene groups, and straight chained and branched propyl, propylene, butyl, and butylene groups. The term $C_{2-6}$ alkenylene as used with respect to Formula XI means groups that contain 2 to 6 carbon atoms and includes straight chained and branched alkenylene groups, in particular ethenylene or the like. In Formula XI, the term $C_{4-6}$ cycloalkyl denotes cyclic groups containing 4 to 6 carbon atoms, namely cyclobutane, cyclopentane, and cyclohexane. In Formula XI, the term halogen as used herein includes fluorine, chlorine, bromine, and iodine. In Formula XI, the term 5- or 6-membered heterocyclic group as used herein includes 5- or 6-membered heterocycloalkyl and heteroaryl groups, e.g., tetrahydrofuranyl, piperidyl, piperazinyl, pyrrolidinyl, morpholinyl, pyridyl, imidazolyl, furyl, and tetrazolyl. In Formula XI, appropriately, $R^0$ represents hydrogen. Alternatively, $R^0$ can represent halogen, in particular fluorine. In Formula XI, $R^1$ may suitably represent any of —$OR^1$, —O—$C_{2-4}$ alkyleneNR$^a$R$^b$, —O—$C_{1-4}$ alkyleneHet and —O—$C_{2-4}$ alkylene-OR$^a$. In particular, $R^1$ represents —O—$C_{2-4}$ alkyleneNR$^a$R$^b$, wherein $C_{2-4}$ alkylene can represent ethylene, and, R$^a$ and R$^b$ can independently represent methyl. Particularly suitably $R^2$ represents hydrogen. Alternatively, in the case where $R^1$ and $R^2$ together form a 3- or 4-membered alkylene or alkenylene chain component of a 5- or 6-membered ring, optionally containing at least one heteroatom as hereinbefore described, $R^1$ and $R^2$ together form a methylenedioxy chain, an ethyleneoxy chain, an ethylenedioxy chain, an ethenyleneoxy chain, a propylene chain, a butylene chain or —NR$^a$ ethylene-O—. Aptly, $R^1$ and $R^2$ together form methylenedioxy, propylene, or —N(CH$_3$)—(CH$_2$)$_2$—O—.

In the above Formula XI, suitably $R^3$ and $R^4$ taken together form a 3- or 4-membered alkylene or alkenylene chain component of a 5- or 6-membered ring, optionally containing at least one heteroatom as hereinbefore described. Particularly $R^3$ and $R^4$ together form a methylenedioxy chain, an ethyleneoxy chain, an ethylenedioxy chain, an ethenyleneoxy chain, a propylene chain, a butylene chain, or —NR$^a$ ethylene-O—. Aptly $R^3$ and $R^4$ together form a methylenedioxy chain, an ethyleneoxy chain, an ethylenedioxy chain, an ethenyleneoxy chain, or a propylene chain. In particular, $R^3$ and $R^4$ together form methylenedioxy or ethyleneoxy, most particularly ethyleneoxy.

A particular subgroup of compounds for use in the methods of the invention include those of the following formula (XII)

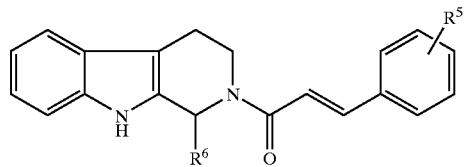

(XII)

wherein
$R^5$ is selected from the group consisting of —OH, —OC$_{2-4}$ alkylene NR$^a$R$^b$, and O—C$_{1-4}$ alkylene Het, wherein Het is as hereinbefore described, and
$R^6$ represents

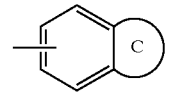

wherein C represents a 5- or 6-membered ring which can be saturated or partially or fully unsaturated, and comprises carbon atoms and optionally one or two heteroatoms selected from oxygen, sulphur and nitrogen, optionally substituted by $C_{1-4}$ alkyl;

and pharmaceutically acceptable salts and solvates (e.g., hydrates thereof).

In that Formula XII, typically, $R^5$ represents —OC$_{2-4}$ alkylene NR$^a$R$^b$, in particular —OCH$_2$CH$_2$N(CH$_3$)$_2$. Alternatively, $R^5$ can represent —O—$C_{1-4}$ alkylene Het, where Het can be piperidyl, pyrrolidinyl (optionally substituted by $C_{1-4}$ alkyl, e.g., methyl) or morpholinyl.

Particularly $R^6$ represents

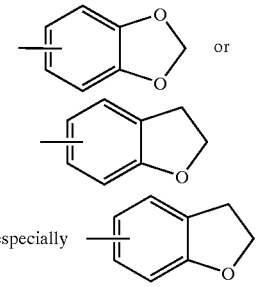

Additional particular compounds for use in the methods of the invention include:
(E)-1-(1-Phenyl-1,3,4,9-tetrahydro-β-carbolin-2-yl)-3-phenylpropene-1-one;
(E)-1-(1-Phenyl-1,3,4,9-tetrahydro-β-carbolin-2-yl)-3-(4-nitrophenyl)propene-1-one;
(E)-1-(1-Phenyl-1,3,4,9-tetrahydro-β-carbolin-2-yl)-3-(4-tifluoromethylphenyl)propene-1-one;
(E)-1-(1-Phenyl-1,3,4,9-tetrahydro-β-carbolin-2-yl)-3-(4-methoxyphenyl)propene-1-one;
(E)-1-[1-(4-Methoxyphenyl)-1,3,4,9-tetrahydro-β-carbolin-2-yl]-3-(4-trifluoromethylphenyl)propene-1-one;
(E)-N-[4-[3-Oxo-3-(1-phenyl-1,3,4,9-tetrahydro-β-carbolin-2-yl)propenyl]phenyl]acetamide;
(E)-1-[1-(4-Methoxyphenyl)-1,3,4,9-tetrahydro-β-carbolin-2-yl)-3-phenylpropene-1-one;
(E)-1-[1-(3,4-Methylenedioxyphenyl)-1,3,4,9-tetrahydro-β-carbolin-2-yl]-3-phenylpropene-1-one;
(E)-1-(1-Phenyl-1,3,4,9-tetrahydro-β-carbolin-2-yl)-3-(4-formylphenyl)propene-1-one;
(E)-N-[4-[3-Oxo-3-(1-(4-nitrophenyl)-1,3,4,9-tetrahydro-β-carbolin-2-yl)propenyl]phenyl]acetamide;
(E)-1-[1-(4-Nitrophenyl)-1,3,4,9-tetrahydro-β-carbolin-2-yl]-3-phenylpropene-1-one;
(E)-1-[1-(4-Trifluoromethoxyphenyl)-1,3,4,9-tetrahydro-β-carbolin-2-yl]-3-phenylpropene-1-one;
(E)-1-[1-(4-Methylphenyl)-1,3,4,9-tetrahydro-β-carbolin-2-yl]-3-phenylpropene-1-one;

(E)-N-[4-[3-Oxo-3-(1-(3,4-methylenedioxyphenyl)-1,3,4,9-tetrahydro-β-carbolin-2-yl)-propenyl]phenyl]acetamide;

(E)-4-[3-Oxo-3-(1-phenyl-1,3,4,9-tetrahydro-β-carbolin-2-yl)-propenyl]benzoic acid, methyl ester;

(E)-1-[1-(2-Chlorophenyl)-1,3,4,9-tetrahydro-β-carbolin-2-yl]-3-phenylpropene-1-one;

(E)-1-(1-Phenyl-1,3,4,9-tetrahydro-β-carbolin-2-yl)-3-(3,4-methylenedioxyphenyl)-propene-1-one;

(E)-1-[1-(3,4-Methylenedioxyphenyl)-1,3,4,9-tetrahydro-β-carbolin-2-yl]-3-(4-bromophenyl)-propene-1-one;

(E)-1-[1-(4-Chlorophenyl)-1,3,4,9-tetrahydro-β-carbolin-2-yl]-3-phenylpropene-1-one;

(E)-1-[1-(3,4-Methylenedioxyphenyl)-1,3,4,9-tetrahydro-β-carbolin-2-yl]-3-(4-ethoxyphenyl)propene-1-one;

(E)-4-[3-Oxo-3-(1-(3,4-methylenedioxyphenyl)-1,3,4,9-tetrahydro-β-carbolin-2-yl)propenyl]acetic acid, phenyl ester;

(E)-1-[1-(3,4-Methylenedioxyphenyl)-1,3,4,9-tetrahydro-β-carbolin-2-yl]-3-(4-hydroxyphenyl)propene-1-one;

(E)-1-[1-(3,4-Methylenedioxyphenyl)-1,3,4,9-tetrahydro-β-carbolin-2-yl]-3-(4-formylphenyl)propene-1-one;

(E)-1-[4-[3-Oxo-3-(1-(3,4-methylenedioxyphenyl)-1,3,4,9-tetrahydro-β-carbolin-2-yl)-propenyl]phenyl]-3-phenylurea;

(E)-1-[1-(3,4-Methylenedioxyphenyl)-1,3,4,9-tetrahydro-β-carbolin-2-yl]-3-(4-aminophenyl)-propene-1-one;

(E)-1-[1-(3,4-Methylenedioxy-phenyl)-1,3,4,9-tetrahydro-β-carbolin-2-yl]-3-(4-nitrophenyl)-propene-1-one;

(E)-1-[1-(3,4-Methylenedioxyphenyl)-1,3,4,9-tetrahydro-β-carbolin-2-yl]-3-[(4-bis(methylsulfonyl)-aminophenyl]-propene-1-one;

(E)-4-[-Oxo-3-[1-(3,4-methylenedioxyphenyl)-1,3,4,9-tetrahydro-β-carbolin-2-yl]-propenyl]benzoic acid, methyl ester;

(E)-N-[4-[3-Oxo-3-[1-(3,4-methylenedioxyphenyl)-1,3,4,9-tetrahydro-β-carbolin-2-yl]propenyl]phenyl]methanesulfonamide;

(E)-4-[3-Oxo-3-[1-(3,4-methylenedioxyphenyl)-1,3,4,9-tetrahydro-β-carbolin-2-yl]propenyl]benzamide];

(E)-4-[3-Oxo-3-[1-(3,4-methylenedioxyphenyl)-1,3,4,9-tetrahydro-β-carbolin-2-yl]-propenyl]benzoic acid;

(E)-1-[1-(3,4-Methylenedioxyphenyl)-1,3,4,9-tetrahydro-β-carbolin-2-yl]-3-(4-cyanophenyl)propene-1-one;

(E)-1-[1-(3,4-Methylenedioxyphenyl)-1,3,4,9-tetrahydro-β-carbolin-2-yl]-3-(4-trifluoromethylphenyl)propene-1-one;

(E)-1-[1-(3,4-Methylenedioxyphenyl)-1,3,4,9-tetrahydro-β-carbolin-2-yl]-3-(3,4-methylenedioxyphenyl)propene-1-one;

(E)-1-[1-(3,4-Methylenedioxyphenyl)-1,3,4,9-tetrahydro-β-carbolin-2-yl]-3-(4-chlorophenyl)-propene-1-one;

(E)-1-[1-(3,4-Methylenedioxyphenyl)-1,3,4,9-tetrahydro-β-carbolin-2-yl]-3-(4-trifluoromethoxyphenyl)propene-1-one;

(E)-1-[1-(3,4-Methylenedioxyphenyl)-1,3,4,9-tetrahydro-β-carbolin-2-yl]-3-(4-methylphenyl)propene-1-one;

(E)-[4-[3-Oxo-3-(1-(3,4-methylenedioxyphenyl)-1,3,4,9-tetrahydro-β-carbolin-2-yl)propenyl]phenyl]urea;

(E)-1-[1-(3,4-Methylenedioxyphenyl)-1,3,4,9-tetrahydro-β-carbolin-2-yl]-3-(4-hydroxymethylphenyl)propene-1-one;

(E)-N-Benzyl-4-[3-oxo-3-(1-(3,4-methylenedioxyphenyl)-1,3,4,9-tetrahydro-beta.-carbolin-2-yl)propenyl]benzamide;

(E)-1-[1-(3,4-Methylenedioxyphenyl)-1,3,4,9-tetrahydro-β-carbolin-2-yl]-3-(2,4-dichlorophenyl)propene-1-one;

(E)-1-[1-(3,4-Methylenedioxyphenyl)-1,3,4,9-tetrahydro-β-carbolin-2-yl]-3-(3-methoxy-4-hydroxyphenyl)propene-1-one;

(E)-1-[1-(3,4-Methylenedioxyphenyl)-1,3,4,9-tetrahydro-β-carbolin-2-yl]-3-(3-hydroxy-4-methoxyphenyl)propene-1-one;

(E)-1-[1-(3,4-Methylenedioxyphenyl)-1,3,4,9-tetrahydro-β-carbolin-2-yl]-3-(4-fluorophenyl)-propene-1-one;

(E)-1-[1-(3,4-Methylenedioxyphenyl)-1,3,4,9-tetrahydro-β-carbolin-2-yl]-3-indan-5-yl-1-propene-1-one;

(E)-N-[4-[3-Oxo-3-(1-(3,4-methylenedioxyphenyl)-1,3,4,9-tetrahydro-β-carbolin-2-yl)propenyl]benzoyl]benzenesulfonamide;

(E)-1-[1-(3,4-Methylenedioxyphenyl)-1,3,4,9-tetrahydro-β-carbolin-2-yl]-3-(3,4-dichlorophenyl)-propene-1-one;

(E)-1-[1-(3,4-Methylenedioxyphenyl)-1,3,4,9-tetrahydro-β-carbolin-2-yl]-3-(3,4-dimethoxyphenol)propene-1-one;

(E)-1-[1-(3,4-Methylenedioxyphenyl)-1,3,4,9-tetrahydro-β-carbolin-2-yl]-3-(3,4-dihydroxyphenyl)propene-1-one;

(E)-N-Methyl-N-[4-[3-oxo-3-(1-(3,4-methylenedioxyphenyl)-1,3,4,9-tetrahydro-β-carbolin-2-yl)propenyl]phenyl]acetamide;

(E)-2,2-Dimethyl-N-[4-[3-Oxo-3-(1-(3,4-methylenedioxyphenyl)-1,3,4,9-tetrahydro-β-carbolin-2-yl)propenyl]phenyl]propionamide;

(E)-1-[1-(3,4-Methylenedioxyphenyl)-1,3,4,9-tetrahydro-β-carbolin-2-yl]-3-(3,5-dimethoxyphenyl)propene-1-one;

(E)-(N)-{4-[3-[1-(3,4-Methylenedioxyphenyl)-6-fluoro-1,3,4,9-tetrahydro-beta-carbolin-2-yl]-3-oxopropenyl]-phenyl}-acetamide;

(E)-1-[1-(3,4-Methylenedioxyphenyl)-1,3,4,9-tetrahydro-β-carbolin-2-yl]-3-(3,4,5-trimethoxyphenyl)propene-1-one;

(E)-N-[4-[3-Oxo-3-(1-(3,4-methylenedioxyphenyl)-1,3,4,9-tetrahydro-β-carbolin-2-yl)propenyl]phenyl]isobutyramide;

(E)-1-[1-(3,4-Methylenedioxyphenyl)-6-fluoro-1,3,4,9-tetrahydro-β-carbolin-2-yl]-3-phenylpropene-1-one;

(E)-N-(2-Methoxyethyl)-4-[3-oxo-3-(1-(3,4-methylenedioxyphenyl)-1,3,4,9-tetrahydro-β-carbolin-2-yl)propenyl]benzamide;

(E)-1-[1-(3,4-Methylenedioxyphenyl)-1,3,4,9-tetrahydro-β-carbolin-2-yl]-3-(3-hydroxyphenyl)propene-1-one;

(E)-1-[1-(3,4-Methylenedioxyphenyl)-1,3,4,9-tetrahydro-β-carbolin-2-yl]-3-(3-methoxyphenyl)propene-1-one;

(E)-1-[1-(3,4-Methylenedioxyphenyl)-1,3,4,9-tetrahydro-β-carbolin-2-yl]-3-(3-nitrophenyl)propene-1-one;

(E)-1-[1-(3,4-Methylenedioxyphenyl)-1,3,4,9-tetrahydro-β-carbolin-2-yl]-3-[4-(2-dimethylaminoethoxy)phenyl]propene-1-one;

(E)-N-(2-Morpholin-4-ylethyl)-4-[3-oxo-3-(1-(3,4-methylenedioxyphenyl)-1,3,4,9-tetrahydro-β-carbolin-2-yl)propenyl]benzamide;

(E)-1-[1-(3,4-Methylenedioxyphenyl)-1,3,4,9-tetrahydro-β-carbolin-2-yl]-3-[4-(1H-tetrazole-5-yl)phenyl]propene-1-one;

(E)-1-[1-(3,4-Methylenedioxyphenyl)-1,3,4,9-tetrahydro-β-carbolin-2-yl]-3-(3-aminophenyl)-propene-1-one;

(E)-N-Cyclohexyl-4-[3-oxo-3-(1-(3,4-methylenedioxyphenyl)-1,3,4,9-tetrahydro-β-carbolin-2-yl)propenyl]benzamide;

(E)-N-(Tetrahydrofuran-2-ylmethyl)-4-[3-oxo-3-(1-(3,4-methylenedioxyphenyl)-1,3,4,9-tetrahydro-β-carbolin-2-yl)propenyl]benzamide;

(E)-1-[1-(3,4-Methylenedioxyphenyl)-1,3,4,9-tetrahydro-β-carbolin-2-yl]-3-(3-cyanophenyl)propene-1-one;

(E)-N-(4-Piperidine-4-carboxylic acid, ethyl ester)-4-[3-oxo-3-(1-(3,4-methylenedioxyphenyl)-1,3,4,9-tetrahydro-β-carbolin-2-yl)propenyl]benzamide;

(E)-N-(4-Piperidine-4-carboxylic acid)-4-[3-oxo-3-(1-(3,4-methylenedioxyphenyl)-1,3,4,9-tetrahydro-β-carbolin-2-yl)propenyl]benzamide;

(E)-3-[3-Oxo-3-[1-(3,4-methylenedioxyphenyl)-1,3,4,9-tetrahydro-β-carbolin-2-yl]-propenyl]benzoic acid (E)-1-[1-(3,4-Methylenedioxyphenyl)-1,3,4,9-tetrahydro-β-carbolin-2-yl]-3-(3-(4-methylpiperazine-1-carbonyl)-phenyl)propene-1-one (E)-N-(2-Piperazin-1-ylethyl)-3-[3-oxo-3-(1-(3,4-methylenedioxyphenyl)-1,3,4,9-tetrahydro-β-carbolin-2-yl)propenyl]benzamide (E)-4-[3-Oxo-3-(1-(3,4-methylenedioxyphenyl)-1,3,4,9-tetrahydro-β-carbolin-2-yl)-propenyl]acetic acid ethyl ester (E)-1-[1-(3,4-Methylenedioxyphenyl)-1,3,4,9-tetrahydro-β-carbolin-2-yl]-3-(3-tetrazolophenyl)propene-1-one (E)-2-[3-Oxo-3-[1-(3,4-methylenedioxyphenyl)-1,3,4,9-tetrahydro-β-carbolin-2-yl]-propenyl]benzoic acid, methyl ester (E)-3-[3-Oxo-3-[1-(3,4-methylenedioxyphenyl)-1,3,4,9-tetrahydro-β-carbolin-2-yl]-propenyl]benzoic acid, methyl ester (E)-1-(4-[3-Oxo-3-(1-(3,4-methylenedioxyphenyl)-1,3,4,9-tetrahydro-β-carbolin-2-yl)-propenyl]phenyl)piperidine-4-carboxylic acid, ethyl ester (E)-N-(1-Ethylpyrrolidin-2-yl-methyl)-3-[3-oxo-3-(1-(3,4-methylenedioxyphenyl)-1,3,4,9-tetrahydro-carbolin-2-yl)propenyl]benzamide (E)-1-[1-(3,4-Methylenedioxyphenyl)-1,3,4,9-tetrahydro-β-carbolin-2-yl]-3-(3-(2-dimethylaminoethoxy)phenyl)propene-1-one (E)-1-[1-(3,4-Methylenedioxyphenyl)-1,3,4,9-tetrahydro-β-carbolin-2-yl]-3-(3,5-diterbutyl-4-hydroxyphenyl)propene-1-one (E)-3-[3-Oxo-3-[1-(4-methoxycarbonylphenyl)-1,3,4,9-tetrahydro-β-carbolin-2-yl]propenyl]benzoic acid, methyl ester (E)-2-[3-Oxo-3-[1-(3,4-methylenedioxyphenyl)-1,3,4,9-tetrahydro-β-carbolin-2-yl]propenyl]benzoic acid (E)-(4-[3-Oxo-3-(1-(3,4-methylenedioxyphenyl)-1,3,4,9-tetrahydro-β-carbolin-2-yl)propenyl]phenoxy)acetic acid, ethyl ester (E)-(4-[3-Oxo-3-(1-(3,4-methylenedioxyphenyl)-1,3,4,9-tetrahydro-β-carbolin-2-yl)-propenyl]phenyl)acetic acid (E)-(4-[3-Oxo-3-(1-(3,4-methylenedioxyphenyl)-1,3,4,9-tetrahydro-β-carbolin-2-yl)propenyl]phenoxy)acetic acid (E)-(1-[1-(3,4-Methylenedioxyphenyl)-1,3,4,9-tetrahydro-β-carbolin-2-yl]-3-(3-nitro-4-chlorophenyl)propene-1-one (E)-1-[1-(3,4-Methylenedioxyphenyl)-1,3,4,9-tetrahydro-β-carbolin-2-yl]-3-(5-nitro-2-chlorophenyl)propene-1-one (E)-3-Chloro-4-[3-oxo-3-[1-(3,4-methylenedioxyphenyl)-1,3,4,9-tetrahydro-beta.-carbolin-2-yl]propenyl]benzoic acid, methyl ester (E)-(4-[3-Oxo-3-(1-(3,4-methylenedioxyphenyl)-1,3,4,9-tetrahydro-β-carbolin-2-yl)propenyl]benzyloxy)acetic acid (E)-1-[1-(3,4-Methylenedioxyphenyl)-1,3,4,9-tetrahydro-β-carbolin-2-yl]-3-(5-amino-2-chlorophenyl)propene-1-one (E)-3-Chloro-4-[3-oxo-3-[1-(3,4-methylenedioxyphenyl)-1,3,4,9-tetrahydro-beta-carbolin-2-yl]propenyl]benzoic acid (E)-1-[1-(3,4-Methylenedioxyphenyl)-1,3,4,9-tetrahydro-β-carbolin-2-yl]-3-(3,5-dibromo-4-hydroxyphenyl)propene-1-one (E)-1-[1-(3,4-Methylenedioxyphenyl)-1,3,4,9-tetrahydro-β-carbolin-2-yl]-3-(4-(2-dimethylaminopropoxy)phenyl)propene-1-one (E)-2-Chloro-5-[3-oxo-3-[1-(3,4-methylenedioxyphenyl)-1,3,4,9-tetrahydro-beta-carbolin-2-yl]propenyl]benzoic acid, methyl ester (E)-1-[1-(3,4-Methylenedioxyphenyl)-1,3,4,9-tetrahydro-β-carbolin-2-yl]-3-(4-(2-diisopropylaminoethoxy)phenyl)propene-1-one (E)-2-Chloro-5-[3-oxo-3-[1-(3,4-methylenedioxyphenyl)-1,3,4,9-tetrahydro-beta-carbolin-2-yl]propenyl]benzoic acid (E)-1-[1-(3,4-Methylenedioxyphenyl)-1,3,4,9-tetrahydro-β-carbolin-2-yl]-3-(3-hydroxy-4-nitro-phenyl)propene-1-one (E)-1-[1-(3,4-Methylenedioxyphenyl)-1,3,4,9-tetrahydro-β-carbolin-2-yl]-3-(3,5-dimethyl-4-hydroxyphenyl)propene-1-one (E)-1-[1-(3,4-Methylenedioxyphenyl)-1,3,4,9-tetrahydro-β-carbolin-2-yl]-3-(3-(2-dimethylaminoethoxy)-4-nitrophenyl)propene-1-one (E)-1-[1-(3,4-Methylenedioxyphenyl)-1,3,4,9-tetrahydro-β-carbolin-2-yl]-3-(3-(2-dimethylaminoethoxy)-4-nitrophenyl)propene-1-one (E)-1-[1-(3,4-Methylenedioxyphenyl)-1,3,4,9-tetrahydro-β-carbolin-2-yl]-3-(3-nitro-4-hydroxy-5-methoxyphenyl)propene-1-one (E)-1-[1-(3,4-Methylenedioxyphenyl)-1,3,4,9-tetrahydro-β-carbolin-2-yl]-3-(3-chlorophenyl)propene-1-one (E)-1-[1-(4-Methoxy-phenyl)-1,3,4,9-tetrahydro-β-carbolin-2-yl]-3-(2-chloro-5-nitrophenyl)propene-1-one (E)-1-[1-(3,4-Methylenedioxyphenyl)-1,3,4,9-tetrahydro-β-carbolin-2-yl]-3-(2,6-dichlorophenyl)propene-1-one (E)-1-[1-(3,4-Methylenedioxyphenyl)-1,3,4,9-tetrahydro-β-carbolin-2-yl]-3-(4-methylaminomethylphenyl)propene-1-one (E)-1-[1-(3,4-Methylenedioxyphenyl)-1,3,4,9-tetrahydro-β-carbolin-2-yl]-3-(3-methylphenyl)propene-1-one (E)-N-Methyl-(4-[3-oxo-3-(1-(3,4-methylenedioxyphenyl)-1,3,4,9-tetrahydro-beta-carbolin-2-yl)propenyl]benzenesulfonamide (E)-1-[1-(3,4-Methylenedioxyphenyl)-1,3,4,9-tetrahydro-β-carbolin-2-yl]-3-(3-hydroxy-4-acetylphenyl)propene-1-one (E)-1-[1-(2,3-Dihydrobenzofuran-5-yl)-1,3,4,9-tetrahydro-β-carbolin-2-yl]-3-(2-chloro-5-nitrophenyl)propene-1-one (E)-1-[1-(3,4-Methylenedioxyphenyl)-1,3,4,9-tetrahydro-β-carbolin-2-yl]-3-(2-hydroxyphenyl)propene-1-one (E)-1-[1-(3,4-Methylenedioxyphenyl)-1,3,4,9-tetrahydro-β-carbolin-2-yl]-3-(3-nitro-2-piperidin-1-ylphenyl)propene-1-one (E)-1-[1-(2,3-Dihydrobenzofuran-5-yl)-1,3,4,9-tetrahydro-β-carbolin-2-yl]-3-phenylpropene-1-one (E)-1-[1-(4-Isopropylphenyl)-1,3,4,9-tetrahydro-β-carbolin-2-yl]-3-(3-nitrophenyl)propene-1-one (E)-1-[1-(2,3-Dihydrobenzofuran-5-yl)-1,3,4,9-tetrahydro-β-carbolin-2-yl]-3-(3-nitrophenyl)propene-1-one (E)-(R)-1-[1-(3,4-Methylenedioxyphenyl)-1,3,4,9-tetrahydro-β-carbolin-2-yl]-3-phenylpropene-1-one (E)-(S)-1-[1-(3,4-Methylenedioxyphenyl)-1,3,4,9-tetrahydro-β-carbolin-2-yl]-3-phenylpropene-1-one (E)-1-[1-(4-Methoxyphenyl)-1,3,4,9-tetrahydro-β-carbolin-2-yl]-3-(3-nitrophenyl)propene-1-one (E)-1-[1-(4-Methylphenyl)-1,3,4,9-tetrahydro-β-carbolin-2-yl]-3-(2-chloro-5-nitrophenyl)propene-1-one (E)-N-(Tetrahydrofuran-2-ylmethyl)-3-[3-oxo-3-(1-(3,4-methylenedioxy)-1,3,4,9-tetrahydro-β-carbolin-2-yl)propenyl]benzamide (E)-1-[1-(Indan-5-yl)-1,3,4,9-tetrahydro-β-carbolin-2-yl]-3-phenylpropene-1-one (E)-1-[1-(3,4-Methylenedioxyphenyl)-1,3,4,9-tetrahydro-β-carbolin-2-yl]-3-(3-acetylphenyl)propene-1-one (E)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one (E)-4-[3-Oxo-3-[1-(4-methoxyphenyl)-1,3,4,9-tetrahydro-β-carbolin-2-yl]propenyl]benzoic acid, methyl ester (E)-1-[1-(3,4-Methylenedioxyphenyl)-1,3,4,9-tetrahydro-β-carbolin-2-yl]-3-(4-methyl-3,4-dihydro-2H-benzo[1,4]-oxazin-6-yl)propene-1-one (E)-1-[1-(3,4-Methylenedioxyphenyl)-1,3,4,9-tetrahydro-β-carbolin-2-yl]-3-(2-hydroxy-5-nitrophenyl)propene-1-one (E)-4-[3-Oxo-3-[1-(2,3-dihydrobenzofuran-5-yl)-1,3,4,9-tetrahydro-β-carbolin-2-yl]propenyl]benzoic acid, methyl ester (E)-4-[3-Oxo-3-[1-(4-methoxyphenyl)-1,3,4,9-tetrahydro-β-carbolin-2-yl]propenyl]benzoic acid (E)-4-[3-Oxo-3-[1-(2,3-dihydrobenzofuran-5-yl)-1,3,4,9-tetrahydro-β-carbolin-2-yl]propenyl]benzoic acid (E)-1-[1-(Benzofuran-5-yl)-1,3,4,9-tetrahydro-β-carbolin-2-yl]-3-phenylpropene-1-one (E)-3-[3-Oxo-3-(1-(3,4-methylenedioxyphenyl)-1,3,4,9-tetrahydro-β-carbolin-2-yl)-propenyl]phenyl)trifluoromethanesulfonic acid, phenyl ester (E)-1-[1-(3,4-Methylenedioxyphenyl)-1,3,4,9-tetrahydro-β-carbolin-2-yl]-3-[4-(2-hyroxyethoxy)phenyl]propene-1-one (E)-1-[1-(Benzofuran-5-yl-1,3,4,9-tetrahydro-β-carbolin-2-yl)]-3-(4-(2-dimethylaminoethoxy)phenyl)propene-1-one (E)-1-[1(3,4-Methylenedioxyphenyl)-1,3,4,9-tetrahydro-β-carbolin-2-yl]-3-(2-dimethylaminophenyl)propene-1-one (E)-1-[1-(3,4-Methylenedioxyphenyl)-1,3,4,9-tetrahydro-β-carbolin-2-yl]-3-(2-piperidin-1-ylphenyl)propene-1-one (E)-4-[3-Oxo-3-[1-(benzofuran-5-yl-1,3,4,9-tetrahydro-β-carbolin-2-yl]-propenyl]-benzoic acid, methyl ester (E)-4-[3-(1-Benzofuran-5-yl-1,3,4,9-tetrahydro-β-carbolin-2-yl)-3-oxo-propenyl]-benzoic acid (E)-4-[3-Oxo-3-(1-(3,4-methylenedioxyphenyl)-1,3,4,9-tetrahydro-β-carbolin-2-yl)propenyl]phenyl)trifluoromethanesulfonic acid, phenyl ester (E)-1-[1-(3,4-Methylenedioxyphenyl)-1,3,4,9-tetrahydro-β-carbolin-2-yl]-3-(2-(2-dimethylaminoethoxy)phenyl)propene-1-one (E)-1-[1-(3-Fluoro-4-methoxyphenyl)-1,3,4,9-tetrahydro-β-carbolin-2-yl]-3-phenylpropene-1-one (E)-(R)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one (E)-[1-(2,3-Dihydrobenzo[1,4]dioxin-6-yl)-1,3,4,9-tetrahydro-β-carbolin-2-yl]-3-phenylpropene-1-one (E)-1-[1-(2,3-Dihydrobenzofuran-5-yl)-1,3,4,9-tetrahydro-β-carbolin-2-yl)]-3-(4-(2-pyrrolidin-1-ylethoxy)phenyl)propene-1-one (E)-1-[1-(3,4-Methylenedioxyphenyl)-1,3,4,9-tetrahydro-β-carbolin-2-yl]-3-[4-pyrrolidin-1-ylphenyl]propene-1-one (E)-(R)-1-[1-(2,3-Dihydrobenzofuran-5-yl)-1,3,4,9-tetrahydro-β-carbolin-2-yl)]-3-(3-nitrophenyl)propene-1-one (E)-1-[1-(3,4-Methylenedioxyphenyl)-1,3,4,9-tetrahydro-β-carbolin-2-yl]-3-[4-imidazol-1-ylphenyl]propene-1-one (E)-4-[3-[1-(2,3-Dihydrobenzo[1,4]dioxin-6-yl)-1,3,4,9-tetrahydro-β-carbolin-2-yl]-3-oxo-propenyl]benzoic acid, methyl ester (E)-1-[1-(2,3-Dihydrobenzo[1,4]dioxin-6-yl)-1,3,4,9-tetrahydro-β-carbolin-2-yl]-3-(3-nitrophenyl)propene-1-one (E)-1-[1-(2,3-Dihydrobenzo[1,4]dioxin-6-yl)-1,3,4,9-tetrahydro-β-carbolin-2-yl)]-3-(4-(2-dimethylaminoethoxy)phenyl)propene-1-one (E)-1-[1-(3-Fluoro-4-methoxyphenyl)-1,3,4,9-tetrahydro-β-carbolin-2-yl)]-3-(4-(2-dimethylaminoethoxy)phenyl)propene-1-one (E)-4-[3-[1-(2,3-Dihydrobenzo[1,4]dioxin-6-yl)-1,3,4,9-tetrahydro-β-carbolin-2-yl]-3-oxopropenyl]benzoic acid (E)-(R)-1-[1-(2,3-Dihydrobenzofuran-5-yl)-1,3,4,9-tetrahydro-β-carbolin-2-yl)]-3-phenylpropene-1-one (E)-(S)-1-[1-(2,3-Dihydrobenzofuran-5-yl)-1,3,4,9-tetrahydro-β-carbolin-2-yl)]-3-(4-2-dimethylaminoethoxy)phenyl)propene-1-one (E)-1-[1-(2,3-Dihydrobenzofuran-5-yl)-1,3,4,9-tetrahydro-β-carbolin-2-yl]-3-(4-aminophenyl)propene-1-one (E)-(S)-1-[1-(2,3-Dihydrobenzofuran-5-yl)-1,3,4,9-tetrahydro-β-carbolin-2-yl]-3-phenylpropene-1-one (E)-(S)-1-[1-(2,3-Dihydrobenzofuran-5-yl)-1,3,4,9-tetrahydro-β-carbolin-2-yl]-3-(3-nitrophenyl)propene-1-one (E)-(R)-1-[1-(2,3-Dihydrobenzofuran-5-yl)-1,3,4,9-tetrahydro-β-carbolin-2-yl)]-3-(4-(1-(S)-methylpyrrolidin-2-ylmethoxy)phenyl)propene-1-one (E)-(R)-1-[1-(2,3-Dihydrobenzofuran-5-yl)-1,3,4,9-tetrahydro-β-carbolin-2-yl)]-3-(3-hydroxyphenyl)propene-1-one (E)-(R)-1-[1-(2,3-Dihydrobenzofuran-5-yl)-1,3,4,9-tetrahydro-β-carbolin-2-yl)]-3-(4-(2-dimethylamino-1-methylethoxy)phenyl)propene-1-one (E)-1-(1-Phenyl-1,3,4,9-tetrahydro-β-carbolin-2-yl)-3-(4-(4-methylpyperazin-1-yl)-phenyl)propene-1-one (E)-(R)-1-[1-(3,4-Methylenedioxyphenyl)-1,3,4,9-tetrahydro-β-carbolin-2-yl)]-3-(4-(1-(S)-methylpyrrolidin-2-ylmethoxy)phenyl)propene-1-one (E)-(R)-1-[1-(3,4-Methylenedioxyphenyl)-1,3,4,9-tetrahydro-β-carbolin-2-yl)]-3-(4-(2-dimethylamino-1-methylethoxy)phenyl)propene-1-one (E)-(R)-1-[1-(3,4-Methylenedioxyphenyl)-1,3,4,9-tetrahydro-β-carbolin-2-yl)]-3-(4-(2-dimethylaminopropoxy)phenyl)propene-1-one (E)-4-[3-Oxo-3-[1-(3,4-fluorophenyl)-1,3,4,9-tetrahydro-β-carbolin-2-yl]propenyl]benzoic acid, methyl ester (E)-(R)-[1-(2,3-Dihydrobenzofuran-5-yl)-1,3,4,9-tetrahydro-β-carbolin-2-yl)]-3-(4-(2-diethylaminoethoxy)phenyl)propene-1-one (E)-(R)1-[1-(2,3-Dihydrobenzofuran-5-yl)-1,3,4,9-tetrahydro-β-carbolin-2-yl)]-3-(4-(2-dimethylaminopropoxy)phenyl)propene-1-one (E)-4-[3-Oxo-3-[1-(3,4-difluorophenyl)-1,3,4,9-tetrahydro-β-carbolin-2-yl]propenyl]benzoic acid (E)-(R)-1-[1-(2,3-Dihydrobenzofuran-5-yl)-1,3,4,9-tetrahydro-β-carbolin-2-yl]-3-(4-aminophenyl)propene-1-one (E)-(R)-1-[1-(3,4-Methylenedioxyphenyl)-1,3,4,9-tetrahydro-β-carbolin-2-yl]-3-(4-aminophenyl)propene-1-one (E)-(R)-1-[1-(3,4-Methylenedioxyphenyl)-1,3,4,9-tetrahydro-β-carbolin-2-yl)]-3-(4-(2-pyrrolidin-1-ylethoxy)phenyl)propene-1-one (E)-(R)-1-[1-(3,4-Methylenedioxyphenyl)-1,3,4,9-tetrahydro-β-carbolin-2-yl)]-3-(4-(2-diethylaminoethoxy)phenylpropene-1-one (E)-1-[1-(3-Fluoro-4-methoxyphenyl)-1,3,4,9-tetrahydro-β-carbolin-2-yl)]-3-(3-nitrophenyl)propene-1-one (E)-(R)-1-[1-(2,3-Dihydrobenzofuran-5-yl)-1,3,4,9-tetrahydro-β-carbolin-2-yl]-3-(4-trifluoromethylphenyl)propene-1-one (E)-(R)-1-[1-(2,3-Dihydrobenzofuran-5-yl)-1,3,4,9-tetrahydro-β-carbolin-2-yl]-3-(3-trifluoromethylphenyl)propene-1-one (E)-(R)-1-[1-(2,3-Dihydrobenzofuran-5-yl)-1,3,4,9-tetrahydro-β-carbolin-2-yl]-3-(4-(2-morpholin-4-ylethoxy)phenyl)propene-1-one (E)-(R)-1-[1-(2,3-Dihydrobenzofuran-5-yl)-1,3,4,9-tetrahydro-β-carbolin-2-yl]-3-(4-(2-(ethylmethylamino)ethoxy)phenyl)propene-1-one (E)-1-[1-(2,3-Dihydrobenzofuran-5-yl)-1,3,4,9-tetrahydro-β-carbolin-2-yl]-3-(4-(3-(dimethylamino)propenyl)phenyl)propene-1-one (E)-(R)-1-[1-(2,3-Dihydrobenzofuran-5-yl)-1,3,4,9-tetrahydro-β-carbolin-2-yl]-3-(4-(3-dimethylamino-2-hydroxypropoxy)phenyl)propene-1-one (E)-(R)-1-(1-(2,3-Dihydrobenzofuran-5-yl)-1,3,4,9-tetrahydro-β-carbolin-2-yl)-3-(4-formylphenyl)propene-1-one (E)-(R)-1-[1-(2,3-Dihydrobenzofuran-5-yl)-1,3,4,9-tetrahydro-β-carbolin-2-yl]-3-(4-propylaminomethyl)phenyl)propene-1-one (E)-(R)-1-[1-(2,3-Dihydrobenzofuran-5-yl)-1,3,4,9-tetrahydro-β-carbolin-2-yl]-3-[4-(2-dimethylaminoethylamino)phenylpropene-1-one (E)-(R)-1-[1-(2,3-Dihydrobenzofuran-5-yl)-1,3,4,9-tetrahydro-β-carbolin-2-yl]-3-(4-(2-aminoethoxy)phenyl)propene-1-one (E)-(R)-1-[1-(2,3-Dihydrobenzofuran-5-yl)-1,3,4,9-tetrahydro-β-carbolin-2-yl]-3-(4-hydroxyphenyl)propene-1-one (E)-(R)-1-[1-(2,3-Dihydrobenzofuran-5-yl)-1,3,4,9-tetrahydro-β-carbolin-2-yl]-3-(4-(4-methylpiperazin-1-yl)phenylpropene-1-one (E)-(R)-1-[1-(2,3-Dihydrobenzofuran-5-yl)-1,3,4,9-tetrahydro-β-carbolin-2-yl]-3-(4-methylaminomethyl)phenyl)propene-1-one (E)-(R)-1-[1-(2,3-Dihydrobenzofuran-5-yl)-1,3,4,9-tetrahydro-β-carbolin-2-yl]-3-(4-isopropylaminomethyl)phenyl)propene-1-one (E)-(R)-1-[1-(2,3-Dihydrobenzofuran-5-yl)-1,3,4,9-tetrahydro-β-carbolin-2-yl]-3-(4-dimethylaminomethyl)phenyl)propene-1-one (E)-(R)-1-[1-(2,3-Dihydrobenzofuran-5-yl)-1,3,4,9-tetrahydro-β-carbolin-2-yl]-3-[4-(3-dimethylaminopropoxy)phenyl]propene-1-one (E)-(R)-1-[1-(2,3-Dihydrobenzofuran-5-yl)-1,3,4,9-tetrahydro-β-carbolin-2-yl]-3-(4-(2-piperidin-1-ylethoxy)phenyl)propene-1-one (E)-1-[1-(3,4-Methylenedioxyphenyl)-1,3,4,9-tetrahydro-β-carbolin-2-yl]-3-(4-(2-piperidin-1-yl-ethoxy)phenyl]propene-1-one (E)-(R)-[2-(4-{3-[1-(2,3-Dihydrobenzofuran-5-yl)-1,3,4,9-tetrahydro-β-carbolin-2-yl]-3-oxopropenyl}-phenoxy)ethyl]methylcarbamic acid, tertbutyl ester (E)-(R)-1-[1-(2,3-Dihydrobenzofuran-5-yl)-1,3,4,9-tetrahydro-carbolin-2-yl]-3-[4-(2-methylaminoethoxy)phenyl]propene-1-one and pharmaceutically acceptable salts and solvates (e.g., hydrates) thereof.

A specific compound of the invention is:

(E)-(R)-1-[1-(2,3-Dihydrobenzofuran-5-yl)-1,3,4,9-tetrahydro-β-carbolin-2-yl)]-3-(4-(2-dimethylaminoethoxy)phenyl)propene-1-one, and pharmaceutically acceptable salts and solvates (e.g., hydrates) thereof.

In another invention embodiment, at least one of the administered delivery compounds or agents is a chemical compound described in the U.S. Pat. Nos. 6,143,757 and 6,001,847. Such preferred compounds are set forth in the following Formula XIII including pharmaceutically acceptable salts thereof.

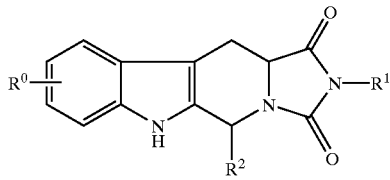

wherein in Formula XIII:
$R^0$ represents hydrogen, halogen, or $C_{1-6}$ alkyl;
$R^1$ is selected from the group consisting of:
(a) hydrogen, (b) $C_{1-6}$ alkyl, optionally substituted with one or more substituents selected from phenyl, halogen, —$CO_2R_a$ and —$NR_aR_b$, (c) $C_{3-6}$ cycloalkyl, (d) phenyl, and (e) a 5- or 6-membered heterocyclic ring containing at least one heteroatom selected from oxygen, nitrogen and sulphur, and being optionally substituted with one or more $C_{1-6}$ alkyl, and optionally linked to the nitrogen atom to which $R_1$ is attached via $C_{1-6}$ alkyl;

$R_2$ is selected from the group consisting of:

(f) $C_{3-6}$ cycloalkyl, (g) phenyl, optionally substituted with one or more substituents selected from —$OR_a$, —$NR_aR_b$, halogen, hydroxy, trifluoromethyl, cyano, and nitro, (h) a 5- or 6-membered heterocyclic ring containing at least one heteroatom selected from oxygen, nitrogen and sulphur; and (i) a bicyclic ring

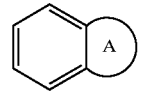

attached to the rest of the molecule via one of the benzene ring carbon atoms, wherein A is a 5- or 6-membered heterocyclic ring as defined in (h); and $R_a$ and $R_b$, independently, represent hydrogen or $C_{1-6}$ alkyl.

In the above Formula XIII, the term "$C_{1-6}$ alkyl" denotes any straight or branched alkyl chain containing 1 to 6 carbon atoms, and includes methyl, ethyl, n-propyl, iso-propyl, n-butyl, pentyl, hexyl, and the like. The term "halogen" denotes fluorine, chlorine, bromine, and iodine.

A particular group of compounds according to Formula XIII are those wherein $R_0$ represents any of hydrogen, methyl, bromine, and fluorine, but the definition of $R_0$ given in Formula XIII includes within its scope other $C_{1-6}$-alkyl and halogen groups.

In Formula XIII above, $R_1$ preferably can represent a substituent selected from methyl, ethyl (optionally substituted by one or more chlorine atoms), butyl, cyclohexyl and benzyl. Other $R_1$ substituents include hydrogen; cycloalkyl groups, such as cyclopropyl; $C_{1-6}$ alkyl, typically ethyl or propyl, substituted by an —$NR_aR_b$ substituent, such as a dimethylamino substituent; phenyl optionally linked to the nitrogen atom to which $R_1$ is attached via a $C_{1-6}$ alkyl chain, such as ethyl or the like; and $C_{1-6}$alkyl, e.g., methyl, substituted by —$CO_2R_a$, such as —$CH_2CO_2Et$ (Et is $CH_2CH_3$) and the like.

Suitable heterocyclic rings within the definition of $R_1$ of Formula XIII include pyridyl, morpholinyl, piperazinyl, pyrrolidinyl, and piperidinyl. Generally, such heterocyclic rings are linked to the nitrogen atom to which $R_1$ is attached via a $C_{1-6}$ alkyl chain, more appropriately a $C_{1-4}$ alkyl chain.

A particular substituent represented by $R_2$ is

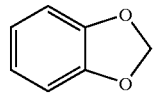

Other $R_2$ substituents include thienyl, pyridyl, furyl, and phenyl, wherein phenyl can be substituted with one or more substituents selected from —$OR_a$ (e.g., methoxy), —$NR_aR_b$ (e.g., dimethylamino), halogen (in particular chlorine or fluorine), hydroxy, trifluoromethyl, cyano, and nitro. Alternatively, $R_2$ can represent a $C_{3-6}$ cycloalkyl group, such as cyclohexyl or the like.

The pharmaceutically acceptable salts of the compounds of Formula XIII that contain a basic center are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconate, methanesulphonate, benzenesulphonate, and p-toluenesulphonate salts. Compounds of Formula XIII also can provide pharmaceutically acceptable metal salts, in particular alkali metal salts, with bases. Examples include the sodium and potassium salts.

It is to be understood that the present invention covers all appropriate combinations of particular and preferred groupings hereinabove.

Additional preferred PDE inhibitor compounds for use in accordance with the invention may be identified by simple testing, such as in by exhibiting an ID50 of less than about 10 mM, preferably less than about 1 mM in an in vitro assay for determining PDE or PDE-5 inhibitory action as disclosed in U.S. Pat. No. 6,100,270; WO-A-93/06104; WO-A-93/07149; WO-A-93/12095; and WO-A-94/00453.

As discussed above, additional permeability agents distinct from a PDE inhibitor can be employed in accordance with the invention. The suitability of any specific additional permeability agent can be readily evaluated by testing the agent to determine if the candidate agent enhances uptake of nucleic acid by targeted tissue relative to a control tissue sample that has not been exposed to the candidate permeability agent. For example, a candidate permeability suitably may provide at least about 10, 20, 30, 40, 50, 60, 70, 80 or 90 percent greater uptake of nucleic acid by targeted tissue relative to a control tissue sample that has not been exposed to the candidate permeability agent. In certain applications, use of a permeability agent having even greater uptake of nucleic acid may be preferred, e.g. where the permeability agent provides at least about 100, 125, 150, 175, 200, 300, 400, 500, 600, 800 or 1000 percent greater uptake of nucleic acid by targeted tissue relative to a control tissue sample that has not been exposed to the permeability agent. It also should be appreciated that the level of nucleic agent uptake that will be suitable for various applications can differ. Thus, for certain applications, lower levels of nucleic acid uptake (e.g. nucleic acid uptake in 2% of cells in a target organ or mass of cells) may be suitable for one application, whereas for other applications, higher levels of nucleic acid uptake (e.g. nucleic acid uptake approaching 90 or 100% of cells in a target organ or mass of cells) may be optimal. The conditions herein described enable graded levels of nucleic acid uptake, e.g. by appropriate varying of type and quantity of permeability agent, virus amount or concentration, and virus exposure time.

Suitable permeability agents and amounts thereof (including PDE inhibitor compounds as well as additional, distinct permeability agents such as serotonin) generally will exhibit good activity in a standard in vitro vasculature permeability assay. For example, permeability agents preferred for at least many applications will include those compounds that exhibit at least about 5%, more preferably at least about 10%, still more preferably at least about 25% or 50% of the permeability activity exhibited by an equivalent molar concentration of bradykinin in a standard vasculature permeability assay, specifically the assay disclosed in R. J. Mullins et al., Journal of Trauma 1989, 29(6):1053–1063. That disclosed assay includes measuring skin lymph flow (LYM FLOW $\mu$l/min) after perfusing a solution containing the permeability agent through specified vasculature of a test animal for a specified period of time. References herein to a standard permeability assay are intended to refer to that protocol and as disclosed in R. J. Mullins, supra.

Specifically suitable amounts of a particular phosphodiesterase inhibitor (PDE) compound(s) and optional distinct permeability agent is exemplified in the example which follows and can be determined by simple testing, e.g. conducting assays as shown in the example which follows to determine at what concentration of a particular PDE inhibitor compound and optional distinct agent are optimal gene transfer realized.

It also should be appreciated that optimal permeability agents and conditions for a particular application may vary with a number of factors such as the specific nucleic acid being administered, the solid cell mass that is being treated and the like. Thus, while histamine may be suitable for many applications of the invention, histamine may be less suitable for certain applications and is excluded from certain aspects of the invention. Again, the suitably of any particular agent can be readily determined by simple testing as discussed above.

Nucleic acid administered in accordance with the invention may be any nucleic acid (DNA or RNA) including genomic DNA, cDNA, rRNA, mRNA and tRNA. These constructs may encode a gene product of interest, e.g. a therapeutic or diagnostic agent. A wide variety of known polypeptides are known that may be suitably administered to a patient in accordance with the invention.

For instance, for administration to cardiac myocytes, nucleic acids that encode vasoactive factors may be employed to treat vasoconstriction or vasospasm. Nucleic acids that encode angiogenic growth factors may be employed to promote revascularization. Suitable angiogenic growth factors include e.g. the fibroblast growth factor (FGF) family, endothelial cell growth factor (ECGF) and vascular endothelial growth factor (VEGF; see U.S. Pat. Nos. 5,332,671 and 5,219,739). See Yanagisawa-Miwa et al., Science 1992, 257:1401–1403; Pu et al., J Surg Res 1993, 54:575–83; and Takeshita et al., Circulation 1994, 90:228–234. Additional agents that may be administered to ischemic heart conditions, or other ischemic organs include e.g. nucleic acids encoding transforming growth factor $\alpha$ (TGF-$\alpha$), transforming growth factor $\beta$ (TGF-$\beta$), tumor necrosis factor $\alpha$ and tumor necrosis factor $\beta$. Suitable vasoactive factors that can be administered in accordance with the invention include e.g. atrial natriuretic factor, platelet-derived growth factor, endothelin and the like. Additional agents that may be administered for the prevention of atrial or ventricular arrhymias include ion channel proteins and/or functionally effective subunits and/or fragments of ion channel proteins that can function to either overexpress or inhibit certain ion currents in the hearts. Further regulatory sequences, such as promoter elements may be added to restrict expression to specific regions of an organ, such as the heart (e.g., atrial natriuretic factor promoter produces preferential expression in the atria relative to the ventricles). Alternatively, regulatory sequences may be added so that expression is regulated up or down by an administered or endogenous compound, such as a hormone.

For treatment of malignancies, particularly solid tumors, nucleic acids encoding various anticancer agents can be employed, such as nucleic acids that code for diphtheria toxin, thymidine kinase, pertussis toxin, cholera toxin and the like. Nucleic acids encoding antiangiogenic agents such as matrix metalloproteases and the like also can be employed. See J. M. Ray et al. *Eur Respir J* 1994, 7:2062–2072.

For other therapeutic applications, polypeptides transcribed by the administered nucleic acid can include growth factors or other regulatory proteins, a membrane receptor, a structural protein, an enzyme, a hormone and the like.

Also, as mentioned above, the invention provides for inhibiting expression or function of an endogenous gene of a subject. This can be accomplished by several alternative approaches. For example, antisense nucleic acid may be administered to a subject in accordance with the invention. Typically, such antisense nucleic acids will be complementary to the mRNA of the targeted endogenous gene to be suppressed, or to the nucleic acid that codes for the reverse complement of the endogenous gene. See J. H. Izant et al., *Science* 1985, 229:345–352; and L. J. Maher II et al., *Arch Biochem Biophys* 1987, 253:214–220. Antisense modulation of expression of a targeted endogenous gene can include antisense nucleic acid operably linked to gene regulatory sequences.

Alternatively, nucleic acid may be administered which antagonizes the expression of selected endogenous genes (e.g. ribozymes), or otherwise interferes with function of the endogenous gene or gene product.

The nucleic acid to be administered can be obtained by known methods, e.g. by isolating the nucleic acids from natural sources or by known synthetic methods such as the phosphate triester method. See, for example, Oligonucleotide Synthesis, IRL Press (M. J. Gait, ed. 1984). Synthetic oligonucleotides also may be prepared using commercially available automated oligonucleotide synthesizers. Also, as is known, if the nucleic acid to be administered is mRNA, it can be readily prepared from the corresponding DNA, e.g. utilizing phage RNA polymerases T3, T7 or SP6 to prepare mRNA from the DNA in the presence of ribonucleoside triphosphates. The nucleotide sequence of numerous therapeutic and diagnostic peptides including those discussed above are disclosed in the literature and computer databases (e.g., GenBank, EMBL and Swiss-Prot). Based on such information, a DNA segment may be chemically synthesized or may be obtained by other known routine procedures such as PCR.

To facilitate manipulation and handling of the nucleic acid to be administered, the nucleic acid is preferably inserted into a cassette where it is operably linked to a promoter. The promoter should be capable of driving expression in the desired cells. The selection of appropriate promoters can be readily accomplished. For some applications, a high expression promoter is preferred such as the 763-base pair cytomegalovirus (CMV) promoter. The Rous sarcoma (RSV) (Davis et al., *Hum Gene Ther,* 1993, 4:151) and MMT promoters also may be suitable. Additionally, certain proteins can be expressed using their native promoter. Promoters that are specific for selected cells also may be employed to limit transcription in desired cells. Other elements that can enhance expression also can be included such as an enhancer or a system that results in high expression levels such as a tat gene or a tar element. A cloning vehicle also may be designed with selective receptor binding and using the promoter to provide temporal or situational control of expression.

The cassette then can be inserted into a vector, e.g. a viral vector such as adenoviruses, adeno-associated virus, retroviruses, herpes viruses (e.g. herpes simplex virus), vaccina viruses, papoviruses, the Sendai virus, the SV40 virus, hybrid viruses, and the like. As mentioned above, adenoviruses are generally preferred. Lytic and semi-lytic viral vectors also can be employed, particularly for administration to malignant cells, such as cells of a solid tumor. Replication-defective recombinant adenoviral vectors, and other suitable vectors, can he produced by known procedures. See Quantin et al., *Proc Natl Acad Sci USA* 1992, 89:2581–2584; Stratford-Perricadet et al., *J. Clin. Invest.* 1992, 90:626–630; and Rosenfeld et al., *Cell* 1992, 68:143–155. The vector also may contain a selectable marker, for instance β-galactosidase (β-gal) or GFP. In general, preparation of vector containing desired nucleic acid for administration to a subject is in accordance with known procedures as disclosed e.g. in Molecular *Cloning, A Laboratory Manual* (2d ed., Sambrook, Fritsch and Maniatis, Cold Spring Harbor 1989); *Current Protocols in Molecular Biology*, (eds. Aufubel et al., Greene Publ. Assoc., Wiley-Interscience, NY, N.Y. 1992); and *Methods in molecular biology* (ed. E J Murray, Humana, Clifton, N.J. 1991). See also the Examples which follow for exemplary procedures.

Naked nucleic acid also may be administered in accordance with the invention, typically formulated with a pharmaceutically acceptable carrier. For example, a polynucleotide, optionally present as a pharmaceutically acceptable salt, can be present in forms such as suspensions, solutions, emulsions in oily or preferably aqueous vehicles that are preferably sterile and pyrogen-free. Pharmaceutically acceptable salts can be suitably prepared from organic or inorganic bases, such as a sodium or potassium salt, or a salt of a primary, secondary or tertiary amine. The administration solution can suitably contain buffers to adjust the pH of the solution, nonionic materials such as sugars e.g. sucrose to adjust tonicity.

Nucleic acid also may be administered as DNA-liposome or RNA-liposome complexes. Such complexes comprise a mixture of fat particles or lipids which bind to DNA or RNA to provide a hydrophobic coated delivery vehicle. Suitable liposomes may comprise any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine or phosphatidylinositol. Synthetic phospholipids also may be used e.g., dimyristoylphosphatidylcholine, dioleoylphosphatidylcholine, dioleoylphosphatidycholine and corresponding synthetic phosphatidylethanolamines and phosphatidylglycerols. Cholesterol or other sterols, cholesterol hemisuccinate, glycolipids, 1,2-bis(oleoyloxy)-3-(trimethyl ammonio)propane (DOTAP), N-[1-(2,3-dioleoyl) propyl]-N,N,N-trimethylammonium chloride (DOTMA), and other cationic lipids may be incorporated into the liposomes.

Typical subjects to which nucleic acid will be administered for therapeutic application include mammals, particularly primates, especially humans, and subjects for xenotransplant applications such as a primate or swine, especially pigs. For veterinary applications, a wide variety of subjects will be suitable, e.g. livestock such as cattle, sheep, goats, cows, swine and the like; poultry such as chickens, ducks, geese, turkeys and the like; and pets such as dogs and cats. For diagnostic or research applications, a wide variety of mammals will be suitable subjects including rodents (e.g. mice, rats, hamsters), rabbits, primates, and swine such as inbred pigs and the like.

The effective dose of nucleic acid will be a function of the particular expressed protein, the target tissue, the subject (including species, weight, sex, general health, etc.) and the subject's clinical condition. The effective dose of nucleic acid also will be a function of the permeability cocktail, which generally will allow less total viral particles to be delivered. Optimal administration rates for a given protocol of administration can be readily ascertained by those skilled in the art using conventional dosage determination tests. Additionally, frequency of administration for a given therapy can vary, particularly with the time cells containing the exogenous nucleic acid continue to produce the desired polypeptide as will be appreciated by those skilled in the art. Also, in certain therapies, it may be desirable to employ two or more different proteins to optimize therapeutic results.

Nucleic acid can be administered to selected tissue by a variety of protocols. The preferred administration method is perfusion of a liquid formulation of the nucleic acid through a solid organ such as a heart or liver or other solid cell mass such as a solid tumor. It may be preferred to recirculate the perfusate through the organ or cell mass which, among other things, can limit delivery of the nucleic acid to targeted cells. A preferred perfusion protocol is described in the Examples which follow. See also Donahue et al., *Proc Natl Acad Sci USA* 1997, 94:4664–4668 for suitable perfusion procedures.

If an adenovirus vector is employed, the nucleic acid preferably is administered in a formulation that is essentially (less than about 5 percent by volume) or completely free of red blood cells which can adsorb adenovirus. Krebs solution is a particularly preferred carrier. Preferably the liquid carrier has a low calcium ion concentration as discussed above. However, other solutions, even native bloodstream with physiologic levels of red blood cells and calcium, can be employed and may be suitable for certain applications, e.g. where the primary intervention for enhancing gene transfer is alteration of vascular permeability.

The concentration of nucleic acid within a liquid carrier can vary, but relatively high concentrations are preferred to provide increase efficiency of nucleic acid uptake as discussed above. More specifically, preferably a viral vector containing nucleic acid for administration is present in a liquid carrier such as Krebs solution at a concentration of about $1 \times 10^8$ plaque forming units (pfu)/ml or greater, more preferably a concentration of about or $5 \times 10^8$, still more preferably a concentration of about $1.0 \times 10^9$ or $1.5~10^9$ pfu/ml or greater.

Flow rates of a perfusate solution containing nucleic acid also can vary, but are preferably relatively rapid compared to normal blood flow in the delivery vessel to provide enhanced nucleic acid uptake. For example, a perfusate flow rate of at least about 5, 10, 15, 20, 25, 50 or 75 percent more rapid compared to normal blood flow in the delivery vessel can be employed. In certain applications, even more rapid flow rates will be preferred, e.g. a perfusate flow rate of at least about 100, 200, 300, 400 or 500 percent more rapid compared to normal blood flow. Flow rates up to 600, 700, 800, 900 or 1000 percent more rapid compared to normal blood flow rate of a subject also can be suitable for certain applications.

It should be appreciated that a particular application of the invention can be readily optimized, e.g. the optimal permeability agents readily selected as discussed above by simple testing against a control; the use of lowered calcium conditions can be readily assessed by testing relative to a control; perfusate flow rates, perfusate concentrations of nucleic acids and the like also all can be readily optimized by testing relative to a control. Optimal conditions and agents may vary from application to application, e.g. for administration to varying organs or mammals of different species.

Nucleic acid can be administered by perfusion by a variety of strategies. Thus, for instance, for an in vivo administration, a catheter delivery protocol can be employed. Such in situ administration can be suitably employed in a procedure solely to deliver the nucleic acid, or in conjunction with a separate surgical procedure such as a peripheral cardiac bypass. A preferred delivery catheter and system is disclosed in WO 9918792A1 (see the figures of that patent publication).

Nucleic acid also may be suitably administered by perfusion through a procedure involving extra-corporal circulation such as performed during coronary artery bypass surgery and aortic valve replacement surgery. In such clinical settings, both arterial and venous vessels can be accessed for delivery, collection and possible recirculation of the perfusate formulation thus targeting gene transfer to the heart and minimizing delivery to remote organs or tissues.

Figure 2A:
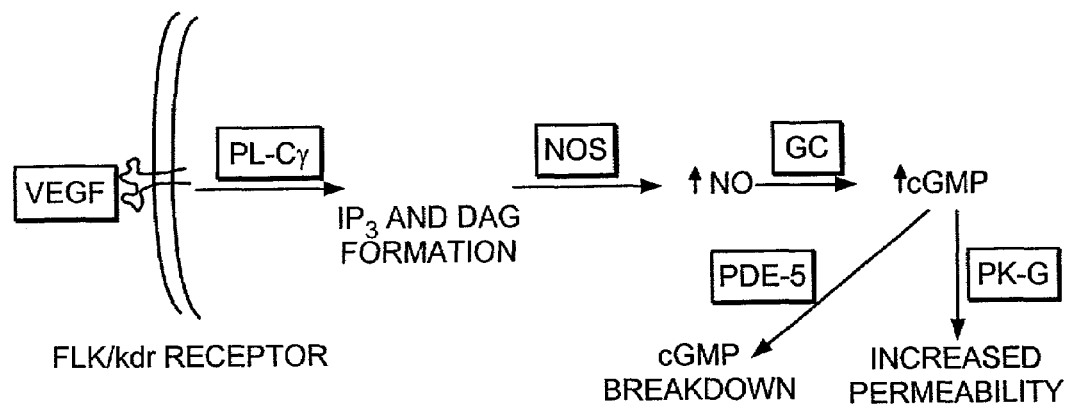
FIG. 2(a) shows a schematic of intracellular pathways mediating increase in vascular permeability and gene transfer.
Figure 2B:
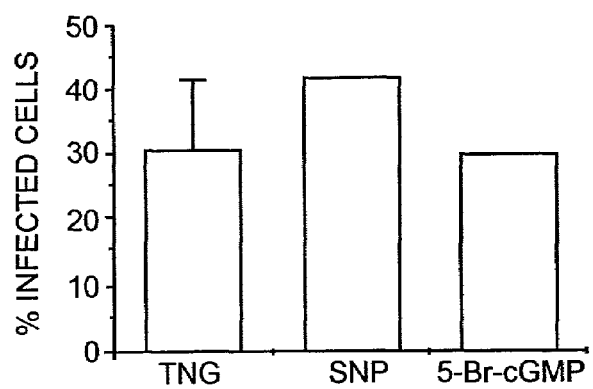
FIG. 2(b) shows the effect of perfusion with nitroglycerin (TNG) or nitroprusside (SNP) or with 5-Br-cGMP on adenovirus-mediated gene transfer. TNG and SNP increase intracellular NO, and 5-Br-cGMP intracellular cGMP. For FIG. 2(a), abbreviations are PL-Cγ: phospholipase C-γ; NOS: nitric acid synthase; PDE-5, phosphodiesterase 5; GC: guanylate cyclase; PK-6: protein kinase G.

Ex vivo perfusion systems also may be employed, particularly in test animals such as a rabbit, rodent, etc. to assess viability and efficiency of specific permeability agents, calcium concentration conditions, cloning vehicles, and perfusion conditions such as flow rate, amount of nucleic acid administered, concentration of nucleic acid in perfusate, etc. An ex vivo procedure also can be employed to deliver therapeutic procedures followed by transplanted of the organ into a patient. A suitable ex vivo system is shown in FIG. 2 of WO 9918792A1.

Alternate ex vivo methods do not involve removal of an intact organ, but rather removal of selected tissue of an organ followed by reimplanting of the tissue after transformation of the removed cells with the desired exogenous nucleic acid. However, as discussed above, such an approach is generally less preferred for the substantial surgical intervention required and difficulty of effective grafting of genetically modified cells.

Additionally, other therapeutic agents, including non-peptide therapeutics, can be administered together with the gene product of the exogenous nucleic acid. Thus, as one example, nitroglycerine may be co-administered to control vasospasms, or an anticancer agent may be co-administered during treatment of malignant cells.

The invention also provides pharmaceutical kits for treatment of a disorder of a subject. Kits of the invention preferably include a delivery system or device to administer the exogenous nucleic acid such as a catheter as discussed above, an ex vivo administration system such as those discussed above, a syringe for injection administration and the like. The kits also will include the nucleic acid to be administered, preferably in a form suitable for administration, e.g. contained in a suitable cloning vehicle such as a viral vector dissolved in desired pharmaceutically acceptable carrier e.g. Krebs solution or other buffered solution that preferably has a low calcium concentration in accordance with the invention and may have other agents such as various buffers, sugars, salts and the like. Alternatively, the nucleic acid may be freeze dried and packaged separately from the fluid carrier. Preferably the nucleic acid and carrier would be present in the kit in optimal dosage quantities. A pharmaceutical kit of the invention also may contain other therapeutic agents that may be co-administered with the gene product of the exogenous gene product as discussed above.

A kit of the invention also preferably contains one or more PDE inhibitor compounds and optional additional, distinct vasculature permeability agents, packaged either separately from or admixed with a liquid formulation to perfuse the one or more agents through a selected area of a subject. The kit also may contain a calcium "washout" formulation to lower the calcium concentration to a desired level in a selected area of a subject. For example, such a "washout" solution could be Krebs solution or other fluid having a low calcium concentration in accordance with the invention and administered prior to administration of the exogenous nucleic acid as discussed above. The one or more permeability agents also may be present in the kit either packaged separately from for later formulation, or pre-formulated with such a low calcium concentration solution for administration prior to delivery of the exogenous nucleic acid. Each of the materials of a kit of the invention, or any composition of the invention that is administered to a subject, particularly a human, should be sterile and otherwise pharmaceutically acceptable. Each of the kit materials intended for administration typically will be stored in a suitable container, preferably each such container hermetically sealed. The kit also suitably may contain written instructions for use and administration of the kit materials.

As discussed above, the invention also provides methods for introducing into a recipient subject transformed donor cells to express a desired gene product in the recipient. Nucleic acid is introduced into the donor cells in accordance with the invention as described herein, i.e. by enhancing vasculature permeability to introduce desired nucleic acid into the cells. Typical recipient subjects for these xenotransplant methods include those subjects disclosed above, i.e. mammals, particularly primates, preferably a human. Donor cells can come from a variety of sources such as from the sources disclosed above. Donor cells from a swine such a pig, or a primate such as a human, are generally preferred. A solid donor organ containing cells comprising exogenous nucleic acid may be transplanted into the recipient subject. Xenotransplant procedures in general have described in the literature such as in U.S. Pat. Nos. 5,650,148 and 5,658,564 and the like.

All documents mentioned herein are incorporated herein by reference.

The following non-limiting example is illustrative of the invention.

General Comments

The following materials and conditions were employed in the following Example 1.

Methods: Quantification of the effect of exposure to vascular permeability mediators was performed using methods reported in the original ROI and patent application as disclosed in WO 9918792A1. This method includes ex vivo perfusion of rabbit hearts with the vascular compounds and with Adgal (a recombinant adenovirus encoding E. coli-galactosidase) followed by enzymatic digestion and isolation of the cardiac myocytes, 48 hr cell culture of the myocytes, and X-gal staining to document gene transfer. The specific methods are as follows:

Adenovirus vectors. Adgal contained the E. coli lac Z gene driven by the human cytomegalovirus (CMV) immediate early promoter. Virus stocks were expanded as previously described,[7] aliquoted in small volumes, and stored in phosphate-buffered saline (PBS) with 10% glycerol at −80° C. Viral titers were determined by the average of two plaque assays performed using a traditional method.[7] Virus stocks were free of replication-competent viruses when tested with a supernatant rescue assay that has the sensitivity to detect one replication-competent virus in $10^9$ recombinant viruses.[8]

Langendorff infection. Rabbit ventricular myocytes were infected as previously described[6]. Adult New Zealand white rabbits (2–3 kg, N=48) received heparin anticoagulation (1000 units IV) prior to pentobarbital (50 mg/kg IV). Each heart was extracted and rinsed twice in ice-cold, modified Krebs buffer containing 138.2 mmol/L Na$^+$, 5.4 mmol/L K$^+$, 1.2 mmol/L Mg$^{2+}$, 1.0 mmol/L Ca$^{2+}$, 144.4 mmol/L Cl$^-$, 1.2 mmol/L SO$_4^{2-}$, 1.2 mmol/L H$_2$PO$_4^-$, 20 mmol/L HEPES, and 15 mmol/L glucose, saturated with O$_2$ at pH 7.4. Next, the aorta was cannulated, and the heart was suspended in an insulated chamber at 35–37° C. During the subsequent experimental manipulations, heart rate, coronary flow and intra-aortic pressure were monitored at 10 minute intervals.

Langendorff perfusion occurred by retrograde flow from the cannula in the ascending aorta to the coronary arteries. Each heart was first perfused with 20 ml Krebs buffer at approximately 30 ml/min. After initial perfusion, the heart was pretreated with one of the following: (1) 15 ml of normal Krebs buffer with $1 \times 10^{-7}$ mol/L substance P over 30 sec, (2) 60 ml of normal Krebs buffer with $1 \times 10^{-9}$ mol/L VEGF over 2 min, (3) 60 ml of normal Krebs buffer with $9 \times 10^{-5}$ mol/L nitroglycerin over 2 min, (4) 60 ml of normal Krebs buffer with $9 \times 10^{-5}$ mol/L sodium nitroprusside over 2 min, (5) 60 ml of normal Krebs buffer with $1 \times 10^{-4}$ mol/L 8-Br-cGMP over 2 min, (6) $1 \times 10^{-5}$ mol/L zaprinast (Sigma), $1 \times 10^{-5}$ mol/L sildenafil (Pfizer), or $1 \times 10^{-6}$ mol/L T-1032 (Tanabe) for 15 min before $3 \times 10^{-10}$ mol/L VEGF for 2 minutes.

Following pretreatment, the heart was infected with Krebs buffer containing the pretreatment compound at the stated concentration and Adgal $1 \times 10^8$ pfu/ml for 2 minutes. During infection, the perfusate was collected and recirculated, and the flow rate was controlled by a peristaltic pump (Masterflex, Cole-Palmer Co.). At the end of the infection interval, the heart was perfused with non-recirculating, virus-free Krebs buffer for a total Langendorff time of 180 minutes. Following the infection and washout phases of the experiments, myocytes were isolated and cultured by perfusing with nominally calcium-free Krebs for 5 minutes at 10–15 ml/min, followed by an enzyme solution consisting of Krebs buffer with 25 mol/L Ca$^{2+}$, 1 mg/ml collagenase B (Boehringer-Mannheim, Indianapolis, Ind.), 0.1 mg/ml protease (fraction XIV, Sigma, St. Louis, Mo.), 60 mmol/L taurine, 8.0 mmol/L glutamic acid, and 2.0 mmol/L d,l-carnitine. After digestion, the ventricles were excised, minced, and agitated by repeated suction through a Pasteur pipette. The resulting cell suspension was strained through a 200 m nylon mesh filter. The ventricles were uniformly digested, and the residue remaining on the filter was from the valvular and tendon structures, with only minimal myocardium. Calcium was gradually repleted in four steps before the cells were added to medium 199 (Mediatech, Herndon, Va.) supplemented with 5.0 mmol/L creatine, 5.0 mmol/L d,l-carnitine, 5.0 mmol/L taurine, 100 u/ml penicillin and 0.1 mg/ml streptomycin, and placed in laminin-coated dishes, in a 37° C. incubator. The myocardial digestion and number of viable cells with each isolation, quantified by counting morphologically normal myocytes, were not affected by any of the experimental manipulations.

In separate control experiments, hearts underwent a sham infection (N=2). None of the cells from these experiments stained positive for -galactosidase activity. Similar negative control data in cultured adult rat ventricular myocytes have been reported.[7] The animals used in this study were maintained in accordance with the guiding principles of the American Physiological Society regarding experimental animals. The experimental protocol was approved by the Institutional Animal Care and Use Committee at the Johns Hopkins University.

Reporter Gene Assays and Data Analysis. Forty-eight hours after exposure to Adgal, the myocytes were fixed in 0.05% glutaraldehyde for 5 minutes at room temperature. The cells were then washed three times in PBS and stained overnight at 37° C. in PBS containing 1.0 mg/ml 5-bromo, 4-chloro, 3-indolyl-D-galactopyranoside (X-gal), 15 mmol/L potassium ferricyanide, 15 mmol/L potassium ferrocyanide and 1 mmol/L $MgCl_2$. Four hundred cells were counted for each experiment. Myocyte survival at 48 hours did not vary with changes in the virus concentration or experimental protocol.

Statistical Analysis. Unless otherwise stated, all experiments were performed in triplicate and the data are presented as mean±s.d. Statistical significance was determined at the 5% level using the unpaired Student's t-test.

EXAMPLE 1

Administration of Substance P and VEGF. Treatment of the ex vivo perfused heart with either $1\times10^{-7}$ M Substance P or $1\times10^{-9}$ M VEGF prior to infection with Adgal results in a significant increase in the percentage infected cells (FIG. 1). These agents increase microvascular permeability faster than either bradykinin or serotonin, and are able to achieve the same enhancement of infection with 2 min of pretreatment that requires 15 min of serotonin exposure.

Treatment with nitroglycerin, nitroprusside, or 8-Br-cGMP. The intracellular pathways that mediate increased vascular permeability after VEGF or Substance P exposure include production of nitric oxide and cGMP.[1-5] Exogenous administration of nitroglycerin or nitroprusside causes an increase in local nitric oxide. Likewise, 8-Br-cGMP is a cGMP analog that is metabolized more slowly than cGMP, causing increases in the effective concentration of cGMP within the cells. Exposure of the ex vivo perfused heart to any of these agents prior to Adgal replicates the increase in infection efficiency caused by VEGF or Substance P administration (FIG. 2).

Figure 3:
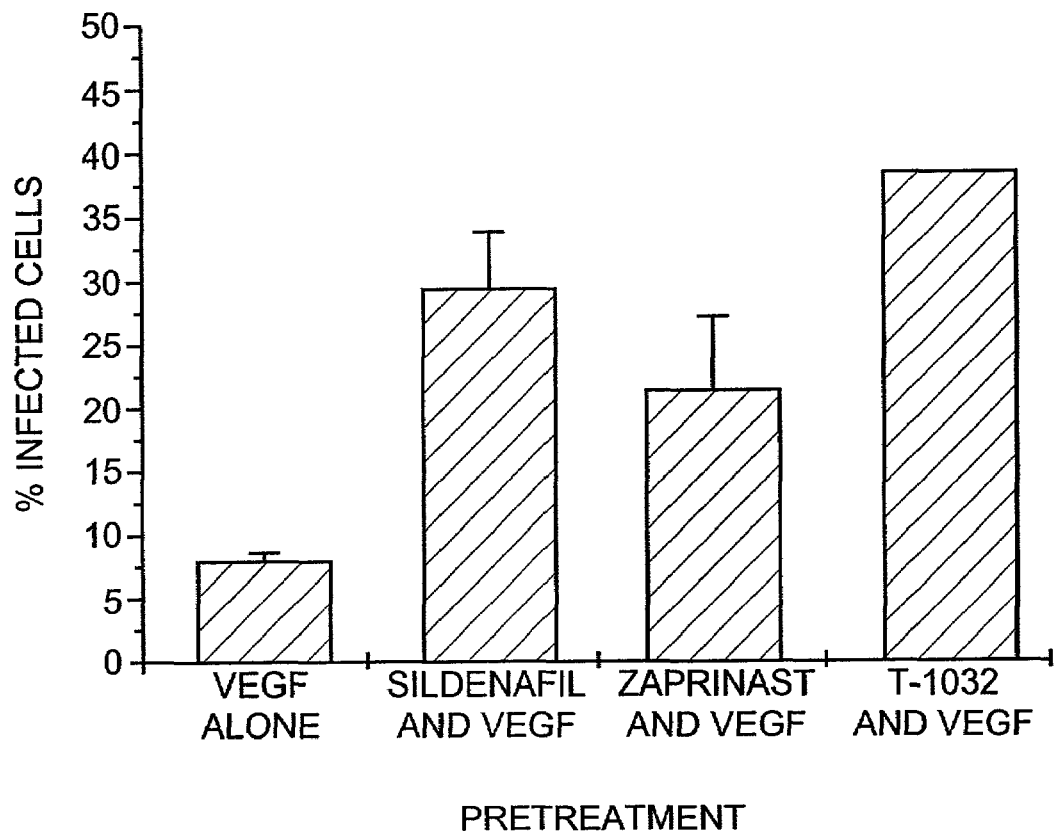
FIG. 3 shows results of the example, particularly gene transfer. Ex vivo perfused hearts were exposed to VEGF ($0.3 \times 10^{-10}$ M, 2 minutes) alone or after 15 minutes exposure to the PDE-5 inhibitors of sildenafil ($1 \times 10^{-5}$ M), zaprinast ($1 \times 10^{-5}$ M) or T-1032 ($1 \times 10^{-6}$ M). Hearts were then exposed to Adβgal ($1 \times 10^{-8}$ pfu/ml, 2 min), and the percentage of cells receiving the transgene quantified. n=3 for each except n=1 for T-1032.

Sildenafil, zaprinast or T-1032 pretreatment before VEGF exposure. Vascular endothelial cells metabolize cGMP using phosphodiesterase-5 (PDE-5).[5-6] Administration of PDE-5 inhibitors was performed prior to VEGF and Adgal exposure to evaluate the effect on infection efficiency. Like the results with 8-Br-cGMP, inhibition of PDE-5 followed by VEGF treatment increased the percentage of infected cells (FIG. 3). No change was seen in the absence of VEGF, indicating that the effect was indeed from PDE-5 inhibition and not a non-specific finding.

These data show increased gene delivery to the intact myocardium. Furthermore, increasing the intracellular concentration of the components of the signalling pathway responsible for the permeability effect improves gene delivery. Taking advantage of this understanding of the intracellular signalling pathways responsible for increasing microvascular permeability, it is shown that use of a PDE-5 inhibitor can particularly delivery effects. Since the exposure time required for VEGF, substance P, 8-Br-cGMP, nitroglycerin or nitroprusside is only 2 minutes and the PDE-5 inhibitors can be given orally or intravenously before the procedure, the current innovations dramatically reduce the pretreatment time before gene delivery.

Results also are disclosed in Nagata et al., J. Mol Cell Cardio, 33: 575–580 (2001), incorporated herein by reference.

The following specific references, also incorporated by reference, are indicated in the examples and discussion above by a number in parentheses.

1. Wu, H. M., Huang, Q., Yuan, Y., and Granger, H. J. VEGF induces NO-dependent hyperpermeability in coronary venules. Amer J Physiol 271:H2735–H2739, 1996.

2. Nguyen, L. S, Villablanca, A. C., and Rutledge, J. C. Substance P increases microvascular permeability via nitric oxide-mediated convective pathways. Am J Physiol R1060–R1069, 1995.

3. Wu, H. M., Yuan, Y., Zawieja, D. C., et al. Role of phospholipase C, protein kinase C, and calcium in VEGF-induced venular hyperpermeability. Am J Physiol 276: H535–H542, 1999.

4. Xia, P., Aiello, L. P., Ishii, H. et al. Characterization of vascular endothelial growth factor's effect on the activation of protein kinase C, its isoforms, and endothelial cell growth. J Clin Invest 98:2018–26, 1996.

5. Hood, J. and Granger, H. J. Protein kinase G mediates vascular endothelial growth factor-induced Raf-1 activation and proliferation in human endothelial cells. J Biol Chem 273:23504–8, 1998.

6. Wallis, R. M., Corbin, J. D., Francis, S. H., and Ellis, P. Tissue distribution of phosphodiesterase families and the effects of sildenafil on tissue cyclic nucleotides, platelet function, and the contractile responses of trabeclae carneae and aortic rings in vitro. Am J Cardiol 83:3C–12C, 1999.

7. Graham F L, Prevec L. Manipulation of adenovirus vectors. In: Murray E J (ed). Methods in Molecular Biology, Vol. 7: Gene Transfer and Expression Protocols. The Humana Press: Clifton, N.J., 1991, pp 109–128.

8. Dion L D, Fang J, Garver R I, Jr. Supernatant rescue assay vs. polymerase chain reaction for detection of wild type adenovirus-contaminating recombinant adenovirus stocks. J Virol Methods 1996; 56: 99–107

This invention has been described in detail with reference to preferred embodiments thereof. However, it will be appreciated that those skilled in the art, upon consideration of this disclosure, may make modifications and improvements within the spirit and scope of the invention.

What is claimed is:

1. A method for delivering nucleic acid to cells in a cardiac tissue comprising:
   administering in vivo to the tissue a cGMP-specific, phosphodiesterase-5 (PDE-5) inhibitor compound and exogenous nucleic acid, wherein the inhibitor is administered prior to or simultaneously with the nucleic acid, and wherein the exogenous nucleic acid is administered by perfusion through vasculature of the cardiac tissue.

2. The method of claim 1 wherein said exogenous nucleic acid encodes a polypeptide.

3. The method of claim 2 wherein the tissue is treated with the phosphodiesterase-5 (PDE-5) inhibitor compound sildenafil to increase vascular permeability.

4. The method of claim 2 wherein the phosphodiesterase-5 (PDE-5) inhibitor compound is a bicyclic heterocyclic compound.

5. The method of claim 2 wherein the phosphodiesterase-5 (PDE-5) inhibitor compound is selected from the group consisting of: a pyrazolo[4,3-d]prymidin-7-one, pyrazolo[3,4-d]pyrimidin-4-one, quinazolin-4-one, purin-6-one, and pyrido[3,2-d]pyrimidin-4-one.

6. The method of claim 2 wherein the phosphodiesterase-5 (PDE-5) inhibitor compound is selected from the group consisting of: sildenafil, zaprinast, and T-1032.

7. The method of claim 2 wherein the tissue is treated with a vascular permeability increasing agent distinct from the phosphodiesterase-5 (PDE-5) inhibitor compound.

8. The method of claim 2 wherein a permeability agent in addition to the phosophodiesterase-5 (PDE-5) compound is administered and said permeability agent is selected from the group consisting of: serotonin, bradykinin, platelet-activating factor, prostaglandin $E_1$, histamine, vascular endothelial growth factor, zona occludens toxin, interleukin-2, plasma kinins, L-N-monomethyl arginine and L-N-nitro-arginine methyl ester.

9. The method of claim 2 wherein the nucleic acid is administered under a calcium ion concentration of about 500 µmol/L or less.

10. The method of claim 2 wherein the tissue is treated with a solution having a calcium ion concentration about 500 µmol/L or less.

11. The method of claim 2 wherein the phosphodiesterase-5 (PDE-5) inhibitor compound is perfused through vasculature of the cardiac tissue prior to administration of the nucleic acid.

12. The method of claim 2 wherein a low calcium ion concentration solution is perfused through vasculature of the cardiac tissue prior to administration of the nucleic acid.

13. The method of claim 2 wherein a fluid having a calcium ion concentration of about 500 µmol/L or less is perfused through vasculature of the cardiac tissue.

14. The method of claim 2 wherein the nucleic acid is administered as a viral vector in a solution at a concentration of about $1 \times 10^8$ pfu/ml or greater.

15. The method of claim 2 wherein the tissue comprises malignant cells.

16. The method of claim 2 wherein the tissue is mammalian.

17. The method of claim 2 wherein the nucleic acid is administered to a human.

18. The method of claim 2 wherein the nucleic acid is administered to an animal selected from the group consisting of: livestock, poultry, dog, and cat.

19. The method of claim 2 wherein the phosphodiesterase-5 (PDE-5) inhibitor compound is a pyrazolo[4,3-d]prymidin-7-one.

20. The method of claim 2 wherein the nucleic acid is administered to the tissue by percutaneous intercoronary delivery.

21. The method of claim 2 wherein the inhibitor is a tetracyclic cGMP specific PDE-5 inhibitor.

22. The method of claim 2 wherein the inhibitor is administered orally.

23. The method of claim 1 wherein the inhibitor is administered orally.

24. The method of claim 1 wherein the nucleic acid is administered to the tissue by perfusion via a catheter.

25. The method of claim 1 wherein the nucleic acid is administered to the tissue by percutaneous intercoronary delivery.

26. The method of claim 1 wherein the nucleic acid is administered by perfusion of the coronary artery.

27. The method of claim 1 wherein the inhibitor is a tetracyclic cGMP specific PDE-5 inhibitor.

28. A method for administering nucleic acid to provide a polypeptide in cells in tissue of interest, comprising:
    treating the tissue with a cGMP-specific, phosphodiesterase-5 (PDE-5) inhibitor compound; and
    subsequently or simultaneously administering exogenous nucleic acid to the tissue, wherein the step of administering is accomplished by ex vivo administration to a solid cell mass selected from the group consisting of a solid organ and a solid tumor.

29. The method of claim 28 wherein the nucleic acid is administered by perfusion.

30. The method of claim 29 wherein the perfusate of nucleic acid is recirculated and then readministered through the organ or cell mass.

31. The method of claim 29 wherein the nucleic acid is administered to the tissue via a catheter.

32. The method of claim 29 wherein the perfusion is via the coronary artery.

33. The method of claim 28 wherein the exogenous nucleic acid is administered ex vivo to a heart.

34. The method of claim 26 wherein the nucleic acid is administered to the tissue by direct injection to myocardium.

35. The method of claim 28 wherein the nucleic acid is administered to the tissue by direct injection.

36. A method for delivering nucleic acid to cells in a tissue of interest, comprising:
    administering to the tissue a cGMP-specific, phosphodiesterase-5 (PDE-5) inhibitor compound and exogenous nucleic acid, wherein the inhibitor is administered prior to or simultaneously with the nucleic acid, and wherein the exogenous nucleic acid is administered by direct injection to a solid cell mass selected from the group consisting of a solid organ and a solid tumor.

37. The method of claim 36 wherein the nucleic acid is administered to the tissue by direct injection to myocardium.

* * * * *